(12) United States Patent
DeArmond

(10) Patent No.: US 7,899,508 B2
(45) Date of Patent: Mar. 1, 2011

(54) INTRACORPOREAL IMPEDANCE AND LEAK MONITORING DEVICE

(75) Inventor: Daniel T. DeArmond, Coralville, IA (US)

(73) Assignee: Board of Regents, The University of Texas System, Austin, TX (US)

(*) Notice: Subject to any disclaimer, the term of this patent is extended or adjusted under 35 U.S.C. 154(b) by 1245 days.

(21) Appl. No.: 11/077,178

(22) Filed: Mar. 10, 2005

(65) Prior Publication Data

US 2005/0240093 A1 Oct. 27, 2005

Related U.S. Application Data

(60) Provisional application No. 60/552,286, filed on Mar. 11, 2004.

(51) Int. Cl.
*A61B 5/00* (2006.01)
(52) U.S. Cl. .................................. 600/327; 600/506
(58) Field of Classification Search ................ 424/551; 600/350, 372, 483; 604/524; 606/8; 607/40, 607/124, 133
See application file for complete search history.

(56) References Cited

U.S. PATENT DOCUMENTS

| | | | |
|---|---|---|---|
| 4,406,878 A * | 9/1983 | DeBoer | 424/9.451 |
| 4,697,593 A * | 10/1987 | Evans et al. | 600/343 |
| 5,357,956 A | 10/1994 | Nardella | 128/642 |
| 5,749,369 A | 5/1998 | Rabinovich et al. | 128/734 |
| 5,823,184 A * | 10/1998 | Gross | 128/204.18 |
| 5,916,171 A * | 6/1999 | Mayevsky | 600/476 |
| 6,360,123 B1 * | 3/2002 | Kimchi et al. | 600/547 |
| 6,425,877 B1 | 7/2002 | Edwards | 604/21 |
| 6,512,949 B1 * | 1/2003 | Combs et al. | 600/547 |
| 7,245,954 B2 * | 7/2007 | Glukhovsky | 600/350 |
| 2003/0216663 A1 * | 11/2003 | Jersey-Willuhn et al. | 600/547 |
| 2004/0133079 A1 * | 7/2004 | Mazar et al. | 600/300 |
| 2004/0254432 A1 * | 12/2004 | Necola Shehada et al. | 600/327 |
| 2005/0124908 A1 * | 6/2005 | Belalcazar et al. | 600/547 |

OTHER PUBLICATIONS

Bruce et al. "Systematic review of the definition and measurement of anastomotic leak after gastrointestinal surgery," British Journal of Surgery, 2001, vol. 88, pp. 1157-1168.

(Continued)

*Primary Examiner*—Nicholas D Lucchesi
*Assistant Examiner*—Gerald Landry, II
(74) *Attorney, Agent, or Firm*—Meyertons, Hood, Kivlin, Kowert & Goetzel, P.C.; Eric B. Meyertons

(57) ABSTRACT

The system and method may measure and monitor physiological changes in a body. In some embodiments, the system and method may measure the impedance at a site in the body. In some embodiments, the system and method identify, quantify, and localize leaks from a site following surgery. In an embodiment, the system includes a flexible conduit with one or more sensors. A flexible conduit shape may be selected to facilitate monitoring of physiological changes in a body and/or detection of leaks at a desired site. In an embodiment, contrast solution may be ingested by, injected in, and/or delivered to a patient. If a leak is present at a site, salt contrast solution may leak from a site and be detected by sensors in a flexible conduit.

22 Claims, 18 Drawing Sheets

OTHER PUBLICATIONS

Heiken et al., "CT Evaluation after Esophagogastrectomy," American Journal of Roentgenology (AJR), 1984, vol. 143, pp. 555-560.

Herrlin, K., "The Diagnosis of Anastomotic Leak After Gastroesophagostomy with Biliary Scintigraphy," Clinical Nuclear Medicine, 1995, vol. 20, pp. 709-711.

Junger et al., "Early detection of anastomotic leaks after colorectal surgery by measuring endotoxin in the drainage fluid," Hepatogastroenterology, 1996, abstract as displayed from PubMed; 1 page.

Marshall et al, "Roux-en-Y Gastric Bypass Leak Complications," Archives of Surgery, 2003, vol. 138, pp. 520-524. (American Meidacl Association).

Ovnat et al., "Early Detection and Treatment of a Leaking Gastrojejunostomy Following Gastric Bypass," Israel Journal of Mecial Sciences, 1986, vol. 22, pp. 556-558.

Sing et al, "Sensitivity and specificity of postoperative upper GI series following gastric bypass," Obesity Surgery, 2003, abstract as displayed from PubMed; 1 page.

\* cited by examiner

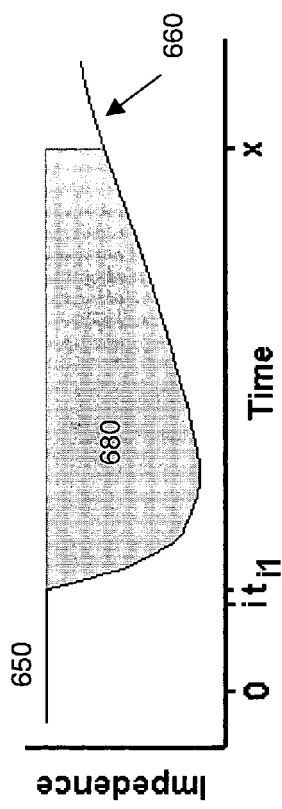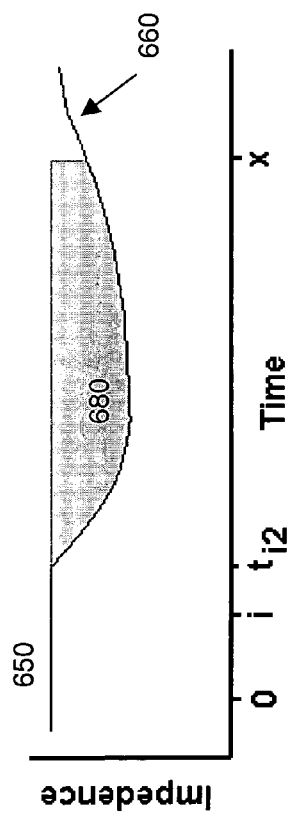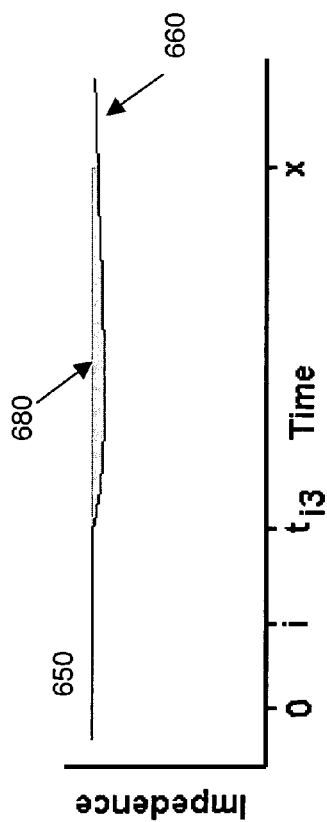

INTRACORPOREAL IMPEDANCE AND LEAK MONITORING DEVICE

PRIORITY CLAIM

This application claims priority to U.S. Provisional Patent Application Ser. No. 60/552,286, filed on Mar. 11, 2004, entitled "Intracorporeal Impedance and Leak Monitoring Device."

BACKGROUND

1. Field of Invention

The present invention relates to systems and methods for measuring and monitoring physiological changes in a body. More particularly, the invention relates to systems and methods for measuring and monitoring intracorporeal leaks in a body.

2. Description of Related Art

Surgery involving the gastrointestinal tract is commonly performed for a variety of reasons. In many cases, gastrointestinal surgery involves the division of the gastrointestinal tract and removal of a segment of the gastrointestinal tract. When the gastrointestinal tract is divided and/or a segment of the gastrointestinal tract is removed, a subsequent re-connection is performed to restore gastrointestinal continuity using suture material, surgical stapling devices, and/or various reinforcing materials. This re-connection is referred to as a gastrointestinal anastomosis.

After gastrointestinal anastomosis operations, leakage of material from the gastrointestinal tract into surrounding tissues or body cavities through the gastrointestinal anastomosis may occur. Leakage may result in significant patient morbidity and mortality due to the fact that gastrointestinal contents generally contain bacteria while the body compartments surrounding the gastrointestinal tract are generally sterile and ill equipped to mount an appropriate immunologic defense against bacterial elements. Ultimately, the tissues of the gastrointestinal tract in the area of an anastomosis undergo regenerative processes that completely seal any areas of potential leakage. In the first few weeks after surgery, while these regenerative processes are occurring, the surgical procedure used to form the anastomosis is expected to establish enough temporary integrity of the gastrointestinal wall to prevent leakage of materials from the gastrointestinal tract into surrounding body compartments. Despite the efforts of surgeons, anastomotic leaks may occur while the tissues undergo regeneration during the first few weeks after surgery.

Gastrointestinal anastomotic leak may also be devastating when it occurs after surgery involving the esophagus or the stomach (i.e., upper gastrointestinal surgery) because leakage from these structures may extend into the chest and specifically into the mediastinum. The mediastinum is vulnerable to a bacteriologic infection, known as mediastinitis. Patients who develop mediastinitis demonstrate very high morbidity and mortality. The leak rate after gastric or esophageal surgery is generally reported to vary from 2-20% of patients. In one large study of 1348 patients who had undergone resection of the esophagus, anastomotic leaks occurred in 52 patients, or 3.9%, and anastomotic leak was associated with a 42.3% mortality rate. Huang, G. J. et al., *Carcinoma of the Esophagus and Gastric Cardia*, Berlin: Springer, 1984, p. 285. In another study of 400 patients who had undergone roux-en-Y gastric bypass operations for morbid obesity, 5.25% of patients developed anastomotic leaks leading to a roughly 10% mortality rate as well as a significantly prolonged hospital stay. Marshall, J. S. et al., "Roux-en-Y gastric bypass leak complications" *Archives of Surgery*, vol. 138, no. 5, May 2003, p. 520-3.

Early identification and treatment of upper gastrointestinal anastomotic leaks may diminish associated morbidity and mortality. Marshall, J. S. et al., "Roux-en-Y gastric bypass leak complications" *Archives of Surgery*, vol. 138, no. 5, May 2003, p. 520-3. Clinicians have proposed numerous methods of identifying anastomotic leak prior to the onset of catastrophic infection; however, no definitive diagnostic test currently exists to establish the presence of anastomotic leak after upper gastrointestinal surgery. Furthermore, surprisingly few studies have objectively examined the sensitivity and specificity of the methods of leak detection. A recent review article presented an examination of the literature concerning anastomotic leaks and concluded that "[t]here is no universally accepted definition of anastomotic leak at any site. The definitions and values used to measure anastomotic failure vary extensively and preclude accurate comparison of rates between studies and institutions," Bruce et al., *British Journal of Surgery*, vol. 88, no. 9, September 2001, pp. 1157-68. The methods of leak detection currently in use, though based on the clinical experience of numerous physicians, are substantiated only by anecdotal data.

Currently, common methods to identify anastomotic leak are: high degree of clinical suspicion; basic clinical parameters exhibited by the patient; and radiographic studies employing upper gastrointestinal contrast agents. Some clinicians rely on clinical suspicion to arrive at the diagnosis of anastomotic leak. Patients at increased risk for anastomotic leak may include: patients who have had prolonged operative times, patients who have undergone repeat operations or operations in which a great deal of scar tissue was encountered during the surgery, patients who have undergone previous radiation to the operative region, and patients in whom a question may have arisen concerning of the quality of the surgical anastomosis due to technical concerns. Clinicians also tend to rely on basic clinical parameters to identify the early stages of a potentially looming catastrophic infection that could be associated with an anastomotic leak. Tachycardia, fever, hypotension, abdominal pain, low urine output, leukocytosis, or even a subjective impression of patient instability all may contribute to making the diagnosis of anastomotic leak. Ultimately, if an anastomotic leak is suspected, the clinician will usually turn to a radiologic study to confirm the presence of the leak prior to taking steps to treat it. Generally, an upper gastrointestinal contrast study is obtained; this involves a radio-opaque contrast material that is swallowed by the patient or otherwise introduced into the upper gastrointestinal tract followed by the performance of a plane radiograph. Computed tomography may be added to this study to help increase the likelihood of detecting a leak Heiken, J. P. et al., "CT evaluation after esophagogastrectomy" *American Journal of Roentgenology*, vol. 143, no. 3, September 1984, pp. 555-60. Many surgeons obtain a routine upper gastrointestinal contrast study between post-operative days 2 to 5 to rule out the presence of an anastomotic leak whether or not the patient manifests clinical evidence of a leak. However, the value of performing upper gastrointestinal contrast studies to identify anastomotic leak has been questioned due to the very low sensitivity and specificity of this study in detecting anastomotic leaks, with some clinicians relying on clinical data alone to make the diagnosis. Singh, R. et al., "Sensitivity and specificity of postoperative upper GI series following gastric bypass" *Obesity Surgery*, vol. 13, no. 1, February 2003, pp. 73-5. Despite the lack of definitive data to defend the use of these methods, they continue to form the basis of current day anastomotic leak detection.

Other methods of diagnosing anastomotic leak have been reported in the medical literature but are not widely employed in clinical practice. One such technique involves the infusion of methylene blue dye into the upper gastrointestinal tract with its subsequent identification in drain effluent material confirmatory of an anastomotic leak. Ovnat, A. et al., "Early detection and treatment of a leaking gastrojejunostomy following gastric bypass" *Israel Journal of Medical Sciences*, vol. 22, no. 7-8, July-August 1986, pp. 556-8. This technique is employed intraoperatively by many surgeons, but is only rarely performed post-operatively to identify anastomotic leak. This pattern of use most likely results from the fact that the technique relies on the visual identification of blue dye extravasation. Intraoperatively, the placement of white towels around the anastomosis prior to infusion of methylene blue dye may improve the surgeon's ability to visually identify extravasated dye, but in the post-operative setting, the identification of blue dye in drain effluent, which may already be significantly discolored by blood or other materials, may be very difficult.

Other techniques that have been described include: measurement of the concentration of endotoxin in drain effluent from around the area of an anastomosis, Junger, W. et al., "Early detection of anastomotic leaks after colorectal surgery by measuring endotoxin in the drainage fluid" *Hepato-Gastroenterology*, vol. 43, no. 12, November-December 1996, pp. 1523-9; and the use of biliary scintigraphy, Herrlin, K., "The diagnosis of anastomotic leak after gastroesophagostomy with biliary scintigraphy" *Clinical Nuclear Medicine*, vol. 20, no. 8, August 1995, pp. 709-11. Currently, these methods are either rarely or never performed in clinical practice.

In summary, anastomotic leak is a major source of morbidity and mortality after upper gastrointestinal surgery that is most effectively treated when it is recognized early. However, no definitive diagnostic test for anastomotic leak exists at the current time and the sensitivity and specificity of the methods currently used have not been adequately determined. Moreover, in the medical literature, authors have pointed to the need for better definition of and identification of anastomotic leaks to improve the care of patients who undergo gastrointestinal surgery. Therefore, there is a recognized need for a device that would provide improved anastomotic leak detection.

SUMMARY

In an embodiment, the physiological change monitoring system may include a flexible conduit with one or more sensors. Flexible conduit is positionable in an opening in a body. Sensors are positioned on a surface of the flexible conduit and are configured to measure impedance. Sensors may measure values other than impedance. Sensors may be positioned on a flexible conduit such that the sensors are in substantially direct contact with a target organ or site. Impedance may be monitored at sites such as the esophagus, lungs, gastrointestinal tract, and/or stomach.

In one embodiment, the physiological change monitoring system is configured to detect leaks at a site in a body. A physiological change monitoring system may include a flexible conduit with one or more sensors. Sensors may be configured to detect changes in impedance. Sensors may be positioned on a flexible conduit such that fluid leaking from a site in the body may contact the sensor. A flexible conduit may have one or more channels. A channel may be a grooved or corrugated portion of a flexible conduit. Flexible conduit may be configured to direct leaking fluid into a channel. Channels may be configured to allow leaking fluid to contact one or more sensors.

In certain embodiments, a physiological change monitoring system is configured to measure impedance at a site in the body and detect fluids leaking from a site. Physiological change monitoring system may include a flexible conduit with one or more sensors. Sensors may be positioned on the inner and outer surfaces of the flexible conduit. Sensors may be positioned on a flexible conduit such that impedance or another value may be measured on an inner surface of the flexible conduit and the outer surface of the flexible conduit. Sensors may be connected to a measurement determining unit. A measurement determining unit may determine whether physiological changes in a body or leaks at a site have occurred.

In an embodiment, leaks may be detected in a body by positioning a physiological change monitoring system in a body. A flexible conduit of a physiological change monitoring system may be positioned proximate a site where a leak may occur. In one embodiment, a contrast solution is ingested or delivered to a patient. Contrast solution passes through the body and if a leak is present, contrast solution may flow from the leak. One or more sensors positioned on a flexible conduit may detect the leaking contrast solution. Sensors may transmit data to a measurement determining unit. Measurement determining unit may produce a signal when the impedance deviates beyond a pre-selected range.

BRIEF DESCRIPTION OF THE DRAWINGS

Advantages of the present invention will become apparent to those skilled in the art with the benefit of the following detailed description of embodiment and upon reference to the accompanying drawings, in which:

FIG. 18a depicts a schematic plot of impedance values obtained by an embodiment of a physiological change monitoring system with three electrode pairs as sensors.

FIG. 18b depicts a schematic plot of impedance values obtained by an embodiment of a physiological change monitoring system with three electrode pairs as sensors.

FIG. 18c depicts a schematic plot of impedance values obtained by an embodiment of a physiological change monitoring system with three electrode pairs as sensors.

Figure 1:
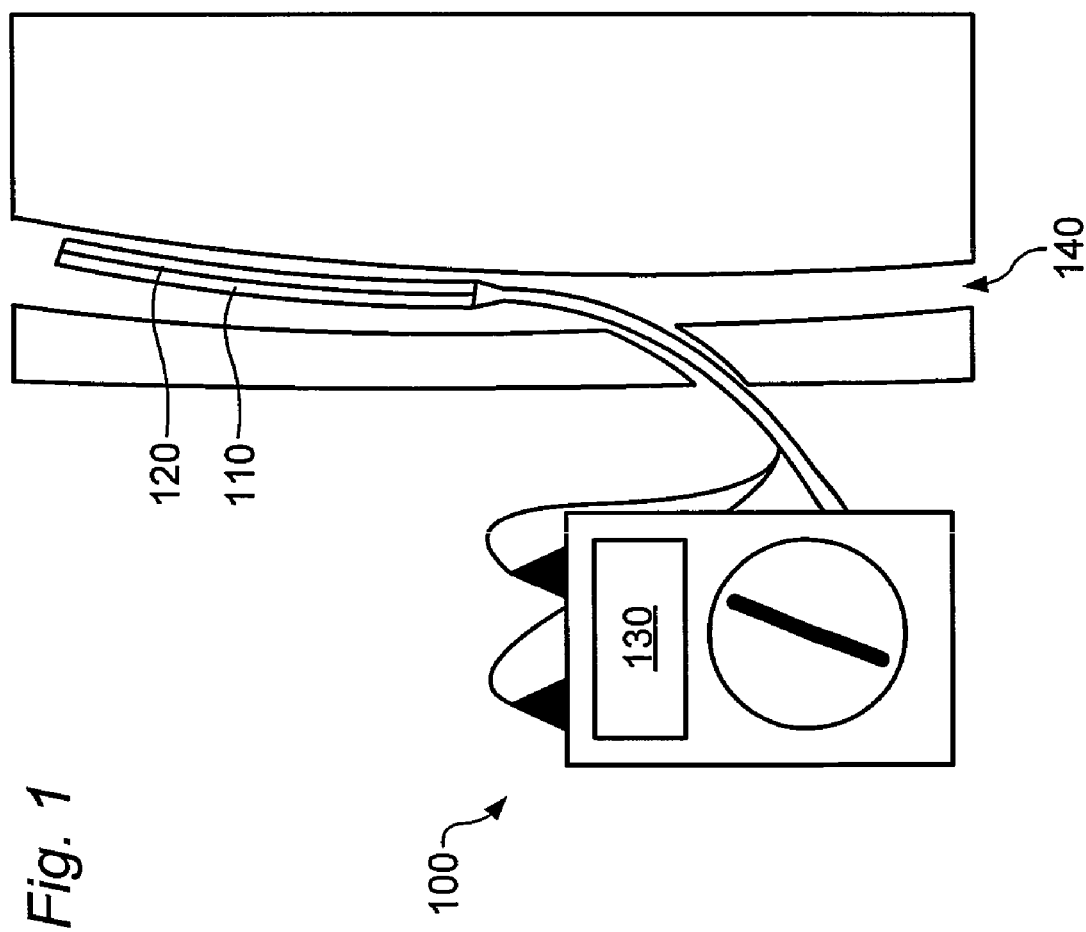
FIG. 1 depicts an embodiment of a physiological change monitoring system.

While the invention is susceptible to various modifications and alternative forms, specific embodiments thereof are shown by way of example in the drawings and will herein be described in detail. It should be understood that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Organs and tissue in a human body possess an ability to conduct electricity due to their biological structures. A body is composed of cells, fluid, and/or air compartments that include a mixture of electrically conductive and resistive elements. The mixture of conductive and resistive elements determines the electrical properties of a given portion of a body. Impedance, in the context of this application, refers to the ability to resist electrical currents. Cells, fluid, and/or air spaces all contribute to the electrical impedance that a given organ or tissue exhibits. When physiological changes occur in a body, changes in cells, fluid, and/or air spaces may occur and the electrical impedance of a portion of a body may be measurably altered. Leaking fluid and/or air from a portion of a body also may be detected by a change in impedance. A physiological change monitoring system may allow precise, minute-by-minute monitoring of changes in a body as manifested by impedance changes. A physiological change monitoring system may allow precise, minute-by-minute monitoring of tissue edema as manifested by tissue impedance.

Herein we describe a system and method for measuring and monitoring physiological changes at a site in the body. In one embodiment, the system and method may measure the impedance at a site in the body. In some embodiments, the system and method may be used to identify and quantify leaks from a site following surgery. In an embodiment, the system includes a flexible conduit with one or more sensors. A flexible conduit may be at least partially positioned in an opening of a body at a site to be monitored. Flexible conduit shape may be selected to facilitate impedance monitoring and/or detection of leaks at a desired site. Sensors may be capable of measuring impedance. In an embodiment, a contrast solution may be ingested by, injected in, and/or delivered to a patient. If a leak is present at a site, contrast solution may leak from a site and be detected by sensors in the flexible conduit.

A physiological change monitoring system may be placed in a body to directly measure physiological changes at a desired organ, tissue, and/or site. In an embodiment, the physiological change monitoring system may directly measure impedance at a desired organ, tissue, and/or site. A site may be any portion of the body. The system may be used in lungs, gastrointestinal tract, or proximate other organs. A physiological change monitoring system may include a measurement determining unit configured to analyze, calculate, and/or display an impedance. A physiological change monitoring system may detect leaks proximate a site. In certain embodiments, a physiological change monitoring system may concurrently determine the presence and/or absence of a leak and impedance at a site. Changes in impedance may indicate changes in physiological conditions.

In some embodiments, as depicted in FIG. 1, a physiological change monitoring system 100 may include a flexible conduit 110. A flexible conduit may include sensors 120 coupled to a measurement determining unit 130. A flexible conduit 110 may be positioned in an opening of a body cavity 140 at a site where potential leaks may occur. A site may be any portion of a body including tissues and organs such as lungs, gastrointestinal tract, and stomach. An operator may visually position flexible conduit in a body cavity. Verification of the position of a flexible conduit may not be necessary. In an embodiment, a flexible conduit may have radio-opaque markers. Radio-opaque markers may be used to indicate if a flexible conduit has moved from its original position.

Flexible conduit (e.g., catheter) may be made of a physiologically inert material. A flexible conduit may be made of latex, silicone, and/or soft plastic. In some embodiments, a flexible conduit may be made of a soft, pliable, and/or insulating material. A flexible conduit may be made of a bioprosthetic material. In an embodiment, a flexible conduit may be formed from a bioprosthetic material such as porcine small intestinal submucosa. A flexible conduit may be at least partially formed from Surgisis, commercially available from Cook Biotech Incorporated. Flexible conduit may be configured to withstand temperature changes. Flexible conduit may be formed of a material that facilitates embedding components in the flexible conduit.

Figure 2:
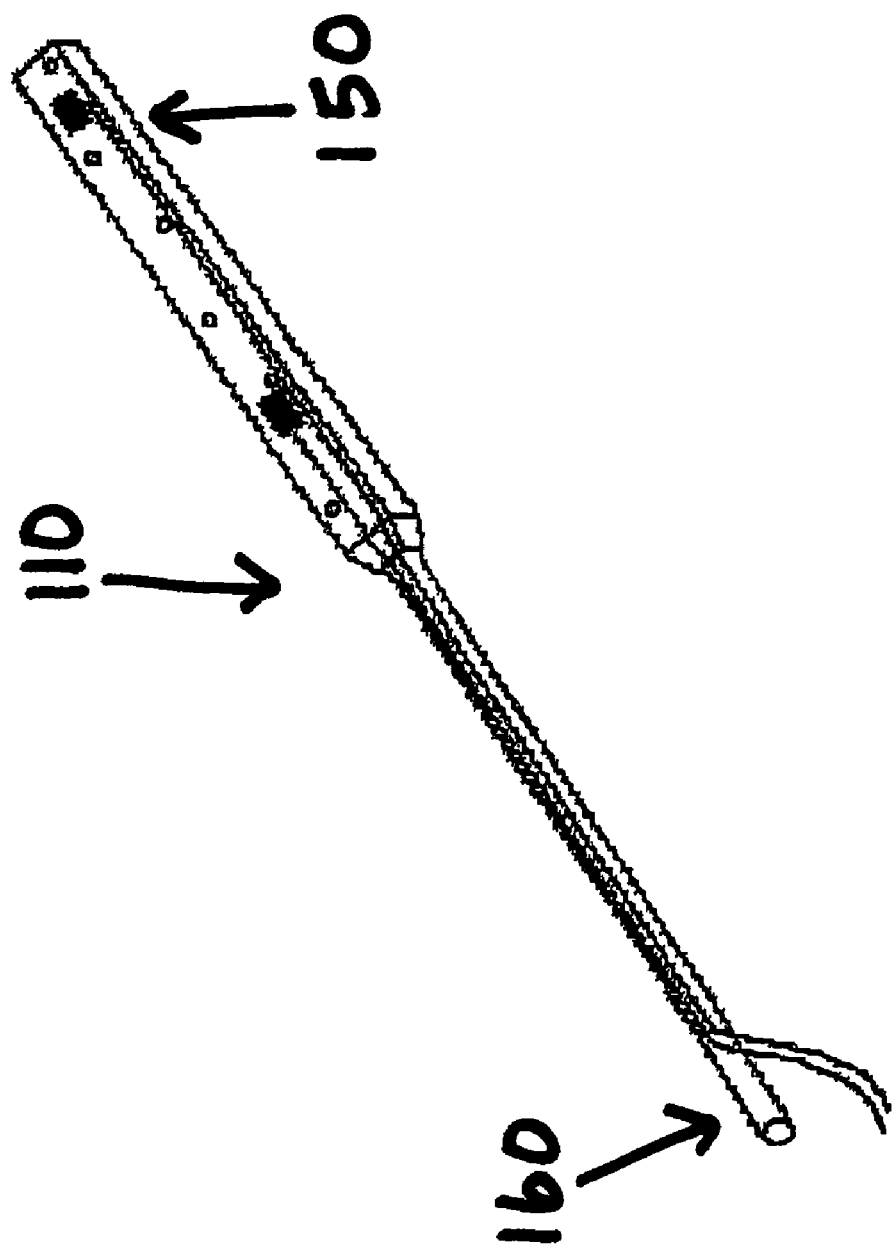
FIG. 2 depicts an embodiment of a flexible conduit of a physiological change monitoring system.

A flexible conduit may have a shape similar to catheters know to one skilled in the art. Flexible conduit may be a double lumen catheter. In some embodiments, flexible conduit may have a substantially circular, substantially oval, substantially rectangular, or irregular cross sectional shape. A flexible conduit 110 may have a substantially rectangular cross-section near a distal end 150 relative a user and a substantially circular cross-section near a proximate end 160 relative a user, as depicted in FIG. 2. A cross-section of flexible conduit may have concave and/or convex portions. A convex cross-sectional shape of flexible conduit may promote contact of a sensor with the surface of a target organ or site in the body to facilitate accurate impedance measurements. In certain embodiments, flexible conduit may have a U-shaped cross-sectional shape. A cross-section of flexible conduit may be teardrop shaped. Fluid in a flexible conduit may flow towards the narrow tip of the tear-shaped cross-section. Flexible conduit may be a tube.

In some embodiments, a flexible conduit may have an adaptable shape. A flexible conduit may be formed from a flexible planar material. The flexible planar material may be wrapped at least partially around a portion of a body. For example, a flexible conduit formed of a flexible planar material may be bent so that the flexible planar material at least partially wraps around an anastomosis. Forming a flexible conduit from a flexible planar material may facilitate collection of all material or fluid leaked from a portion of a body. Leak detection may be enhanced by bending a flexible planar material so that it at least partially surrounds a portion of a body.

In some embodiments, a flexible conduit may include a channel. A channel may be configured to increase the probability that a sensor positioned in the channel may contact fluid leaking from a site. A flexible conduit may be configured to direct the flow of fluid from a leak to a channel in the flexible conduit. A channel may be a groove. A channel may be a corrugated section of a flexible conduit.

In some embodiments, flexible conduit may have a smaller diameter at a proximal end, relative to an operator, relative to the diameter of the distal end of the flexible conduit. In certain embodiments, a flexible conduit may include two or more pieces coupled together. A retracting conduit may be coupled to a catheter. Retracting conduit may be rigidly bonded to the catheter. In an embodiment, a retracting conduit may be a portion of a flexible conduit. A retracting conduit may be made of a soft, pliable, insulating, and/or inert material. Retracting conduit may be made of latex, silicone, soft plastic, and/or any other suitable material. A retracting conduit and a flexible conduit may be made of similar materials.

Retracting conduit may have a smaller diameter than a flexible conduit. A retracting conduit may have a similar diameter to a flexible conduit. Flexible conduit may be positioned substantially in a body cavity and retracting conduit may be at least partially positioned in the body cavity. Retracting conduit may exit a body via an opening in the skin and musculature of the body. In an embodiment, retracting conduit is configured to be positionable partially inside a body cavity and partially outside a body cavity. An operator may use retracting conduit to remove a physiological change monitoring system manually without requiring an additional surgical operation.

In an embodiment, flexible conduit is a catheter positioned in a body cavity containing a gastrointestinal anastomosis and retracting conduit exits the patient via a puncture hole created at the time of surgery through the skin and musculature of the involved body cavity (e.g., abdomen, neck, or thorax). An operator may remove the catheter by withdrawing the retracting conduit from the body cavity. A catheter coupled to a retracting conduit may be removed simultaneously.

A physiological change monitoring system may include one or more sensors. Sensors may be positioned on a surface of a flexible conduit. In an embodiment, sensors may be positionable such that a sensor may directly contact a site in a body. Sensors may be electrodes. Sensors may be configured to monitor impedance and/or detect changes in impedance. In certain embodiments, sensors may measure values other than impedance (e.g., pH, oxygen levels, ion concentration, light absorption, etc.) and are connected to a corresponding measurement determining device. In an embodiment, measurement determining unit may include a device capable of measuring impedance. Measurement determining units may include, but are not limited to, devices for measuring pH, oxygen levels, ion concentration, light absorbtion, and/or other receiver units. In an embodiment, a sensor may detect oxygen. A sensor may be an IR sensor. In an embodiment, a patient may ingest an IR absorbing contrast solution. A sensor may detect the presence of the IR absorbing contrast solution in the physiological change monitoring system. Sensors may also include: pH sensors; ion concentration sensors; light probes; ion selective field effect transistors, such as those commercially available from Sphere Medical; microsensors; metabolite sensors; molecularly-imprinted-polymer-biosensors; photodetectors; detectors of radioactivity; pizoelectric-crystal transmitter/receiver units and/or chemical sensors on silicon chips. Monitoring pH in a body may be desirable in vascular surgery, lower extremity surgery, kidney surgery, lung surgery, gastrointestinal surgery, neurosurgery, and/or transplants.

One or more sensors may be coupled to flexible conduit. Sensors may be bonded to flexible conduit. Sensors may be glued to flexible conduit. In an embodiment, sensors are at least partially embedded in flexible conduit. Sensors may have a smooth surface. Sensors may be positioned on the distal end of a flexible conduit relative to a user. In some embodiments, the selected site for leak detection or impedance monitoring may determine the position of sensors on a flexible conduit.

In certain embodiments, sensors may be embedded in the material of a flexible conduit such that a sensor may not contact another sensor. Sensors may be configured such that only one surface of a sensor is exposed (e.g., only one surface of the sensor is exposed to a site.). In an embodiment, the exposed surface of a sensor may be positioned on a concave surface of a flexible conduit. The configuration of sensors on a flexible conduit may promote contact of exposed faces of sensors with a target organ or tissue. In an embodiment, sensors may be embedded in a flexible conduit such that the two opposing faces of a sensor may take measurements. In an embodiment, flexible conduit may have an opening configured to hold a sensor. A sensor may measure impedance or other values at the inner surface of a flexible conduit and the outer surface of the flexible conduit.

Sensors may be coupled to wires that are completely or partially embedded in a flexible conduit. In an embodiment, flexible conduit may be a double lumen catheter and wires may be positioned in the outer lumen of the catheter while leaking fluids may flow through an inner lumen. Wires may connect one or more sensors to a measurement determining unit. Sensors may transmit data to a measurement determining unit. A measurement determining unit may produce a signal when the impedance deviates beyond a pre-selected range. Measurement determining unit may be any device capable of analyzing data from a sensor. A measurement determining unit may be an impedance monitoring unit. In an embodiment, measurement determining unit may be a voltmeter. Alternatively, a measurement determining unit may be an ion detector. Wires may exit a body cavity via retractor conduit and exit the retractor conduit via an opening in the retractor conduit. An opening in the retractor conduit may be at an end, proximate an end, or at any other position along the length of the retractor conduit. In an embodiment, wires may be at least partially embedded in a retractor conduit. Wires may be configured to resist damage from fluids in a body cavity. At least partially embedding wires may diminish damage to the wires due to contact with fluids in a body cavity. In an embodiment, wires may be coated with a corrosion resistant material.

In some embodiments, a sensor may be positioned at a bottom of the "U" in a U-shaped cross-section flexible conduit. A sensor may be positioned about 1 cm to about 2 cm below a potential leak in a body cavity. A sensor may be positioned at a midpoint of a flexible conduit. Flexible conduit may be positioned at the time of surgery proximate a gastrointestinal anastomosis such that a sensor lies directly behind the anastomosis and the trough-shape of the flexible conduit is cupped around the anastomosis. The length of the catheter may be configured to be slightly larger than a circumference of the anastomosis. Since a flexible catheter may be at least partially molded around the circumference of the gastrointestinal tissues surrounding the anastomosis, the flexible conduit may have proximity to areas of potential leaks.

In an embodiment of a flexible conduit with a U-shaped cross-section, sensors, which may be located at the bottom of the trough, do not directly contact the tissues of the anastomosis. The trough or U-shape of a flexible conduit may be configured to pool and/or direct leaked salt contrast solution over one or more sensors. The material, length, and shape of a flexible conduit, the position of a flexible conduit relative to the anastomosis, and the position of sensors within a flexible conduit may be optimized to maximize the possibility of a sensor contacting a leak and, as such, maximize the probability of detecting an anastomotic leak.

Dimensions of a flexible conduit 110 may vary depending on the site in the body of intended use. As depicted in FIGS. 3a-3f, in some embodiments, length 170, width 180, height 190 and thickness 200 of a flexible conduit 110, may be about 15 cm×2 cm×1 cm×0.5 cm respectively. Length 170 of flexible conduit 110 may be about 5 cm to about 50 cm. Width 180 of flexible conduit 110 may be about 0.5 cm to about 5 cm. Height 190 of flexible conduit 110 may be about 0.25 cm to about 5 cm. Thickness 200 of the flexible conduit 110 may be about 0.1 cm to about 2 cm. Length and diameter of a proximal end 160 of a flexible conduit 110 may be about 90 cm×0.5 cm respectively. In an embodiment, length, width and depth of sensors 120 may about 0.5 cm×0.3 cm×0.2 cm respectively. A length of a sensor 120 may be about 0.1 cm to about 5 cm. A width of a sensor 120 may be about 0.1 cm to about 5 cm. A depth of a sensor may be about 0.05 cm to about 2 cm. Any distance may separate sensors from each other. In an embodiment, a distance between two sensors 120 may be about 0.5 cm. A distance between two sensors 120 may be at least 0.5 cm. A distance from distal end 150 of a flexible conduit 110 to point 210 at which wires from sensors exit may be about 10 cm. Wires may exit flexible conduit 110 at a point 210 between about 3 cm to about 20 cm from a distal end 150 of the flexible conduit.

Figure 3:
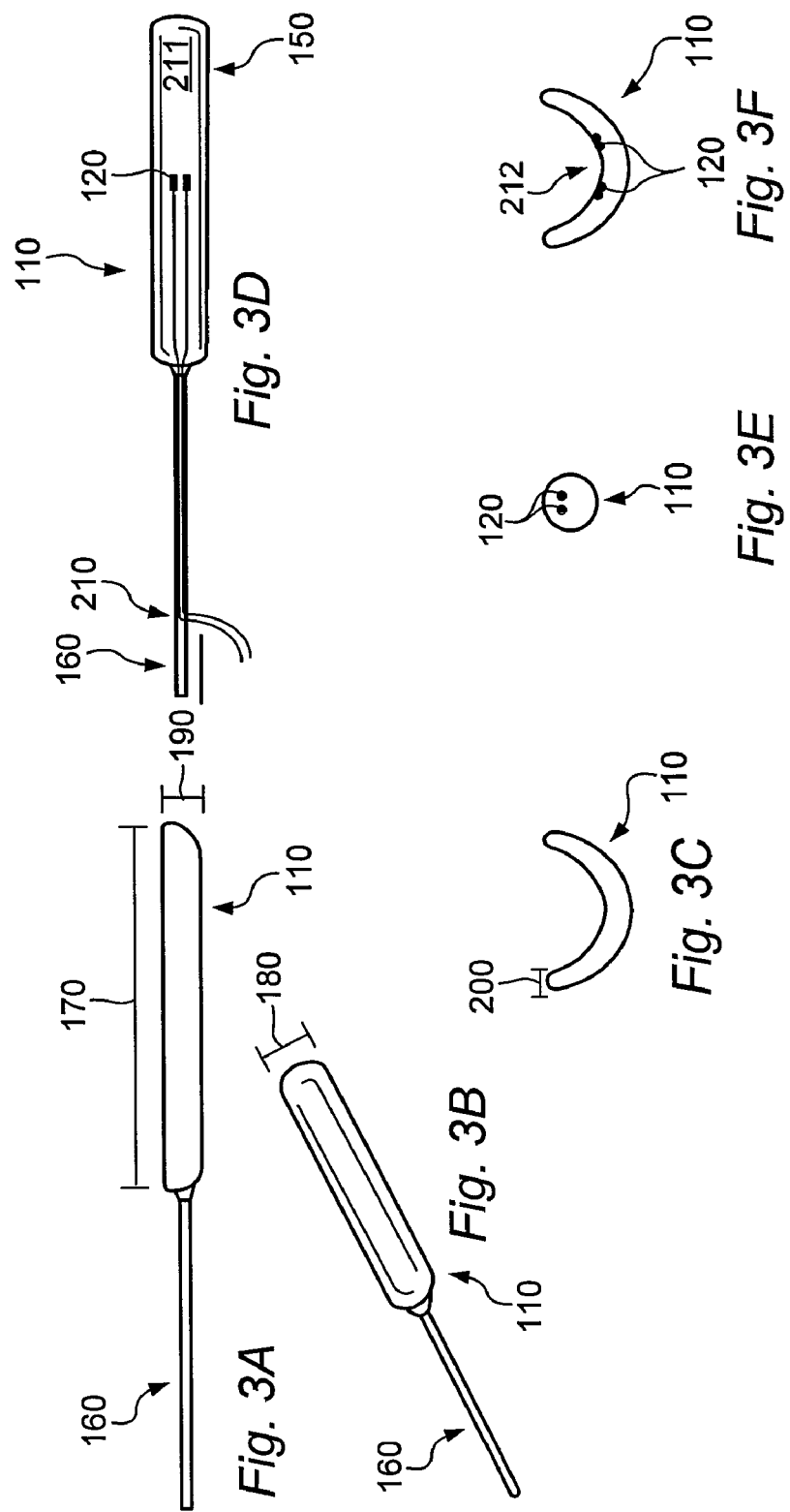
FIG. 3*a* depicts a side view of an embodiment of a physiological change monitoring system.
FIG. 3*b* depicts a top view of an embodiment of a physiological change monitoring system.
FIG. 3*c* depicts a cross-sectional view of an embodiment of a physiological change monitoring system.
FIG. 3*d* depicts a side view of an embodiment of sensors in a flexible conduit.
FIG. 3*e* depicts a cross-sectional view of an embodiment of sensors in a flexible conduit.
FIG. 3*f* depicts a cross-sectional view of an embodiment of sensors positioned in a U-shaped flexible conduit.

FIGS. 3a-3c depict respective side, top, and cross-sectional views of an embodiment of a physiological change monitoring system. Flexible conduit 110 of a physiological change monitoring system may have a U-shaped cross-section as seen from the top view and cross-sectional view. FIG. 3d in conjunction with FIGS. 3e and 3f depicts a schematic diagram of an embodiment of sensors 120 in a flexible conduit 110. A sensor 120 may be positioned on a surface of a flexible conduit 110. A sensor may be positioned on a surface in direct contact with a site and/or organ. A sensor 120 may be positioned in the bottom of the "U" in a U-shaped flexible conduit 110 such that fluid leaking from a site may travel along the bottom of the "U" and contact the sensor. In some embodiments, sensor 120 may be positioned in a channel 211 in flexible conduit 110, where the channel may be configured such that fluid leaking from a site travels down the channel.

Sensors 120 may include a pair of electrodes, as seen from the top and cross-sectional view, in FIGS. 3d-3f. Sensors 120 may be at least partially embedded in flexible conduit 110. Sensors 120 may be embedded in flexible conduit 110 such that the sensors occupy a bottom of trough 212 of flexible conduit and top surfaces of the sensors are flush with a surface of the flexible conduit.

Figure 4:
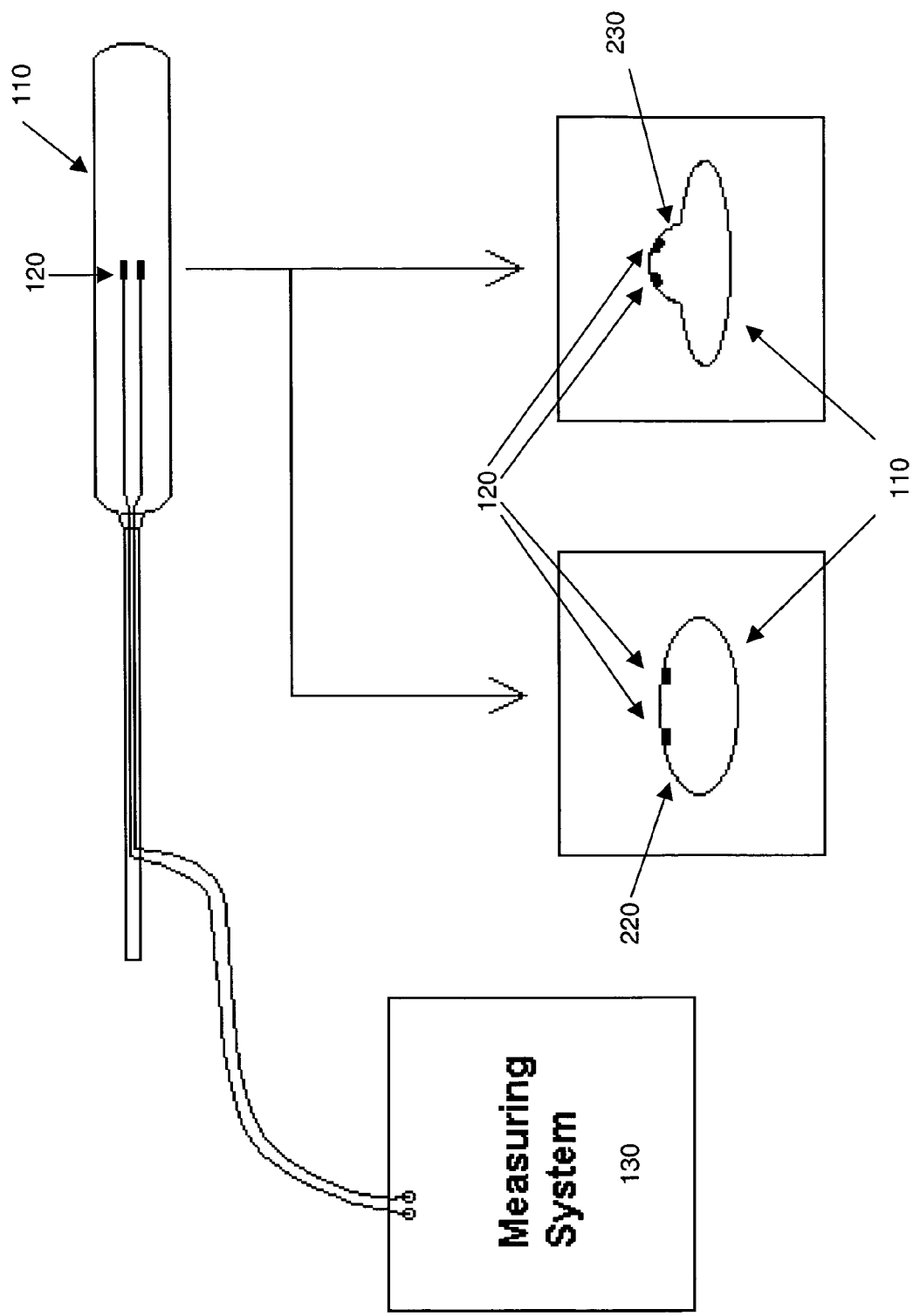
FIG. 4 depicts an embodiment of a physiological change monitoring system.

FIG. 4 depicts an embodiment of a flexible conduit 110 with an oval-shaped cross-section. Sensors 120 may be positioned on the elongated side 220 of the cross-section. FIG. 4 depicts a cross-sectional view of an embodiment of a flexible conduit 110. Flexible conduit 110 may have an oval-shaped cross-section with a protruding portion 230 on one side. Sensors 120 may be positioned on the protruding portion 230. In FIG. 4, a pair of sensors 120 may be at least partially embedded in flexible conduit 110. Sensors 120 may be connected to separate wires that may be at least partially embedded in flexible conduit 110. In an embodiment, wires may be embedded along a length of flexible conduit 110. Wires may exit flexible conduit 110 at a desired location. Wires may exit flexible conduit 110 near a proximal end of the flexible conduit. Wires may be configured to be coupled to a measurement determining unit 130, such as an impedance measuring unit. A measurement determining unit and sensors may be adapted for the use in various physiological change measuring methods known in the art, including but not limited to impedance determining methods using high frequency modulated currents or current pulses and methods using various test current pulses.

As depicted in FIG. 4, in some embodiments, sensors 120 may be embedded in a flexible conduit 110 such that the sensors may not contact other sensors. In an embodiment, only one of the surfaces of each sensor is exposed. An exposed surface of each sensor 120 may be positioned on the convex surface 220 of flexible conduit 110. In an embodiment, sensors 120 may be positioned on the convex surface of a protrusion 230 extending from flexible conduit 110. The arrangement of sensors on a surface of flexible conduit may be configured to promote contact of an exposed surface of a sensor with a target organ or site.

Figure 5:
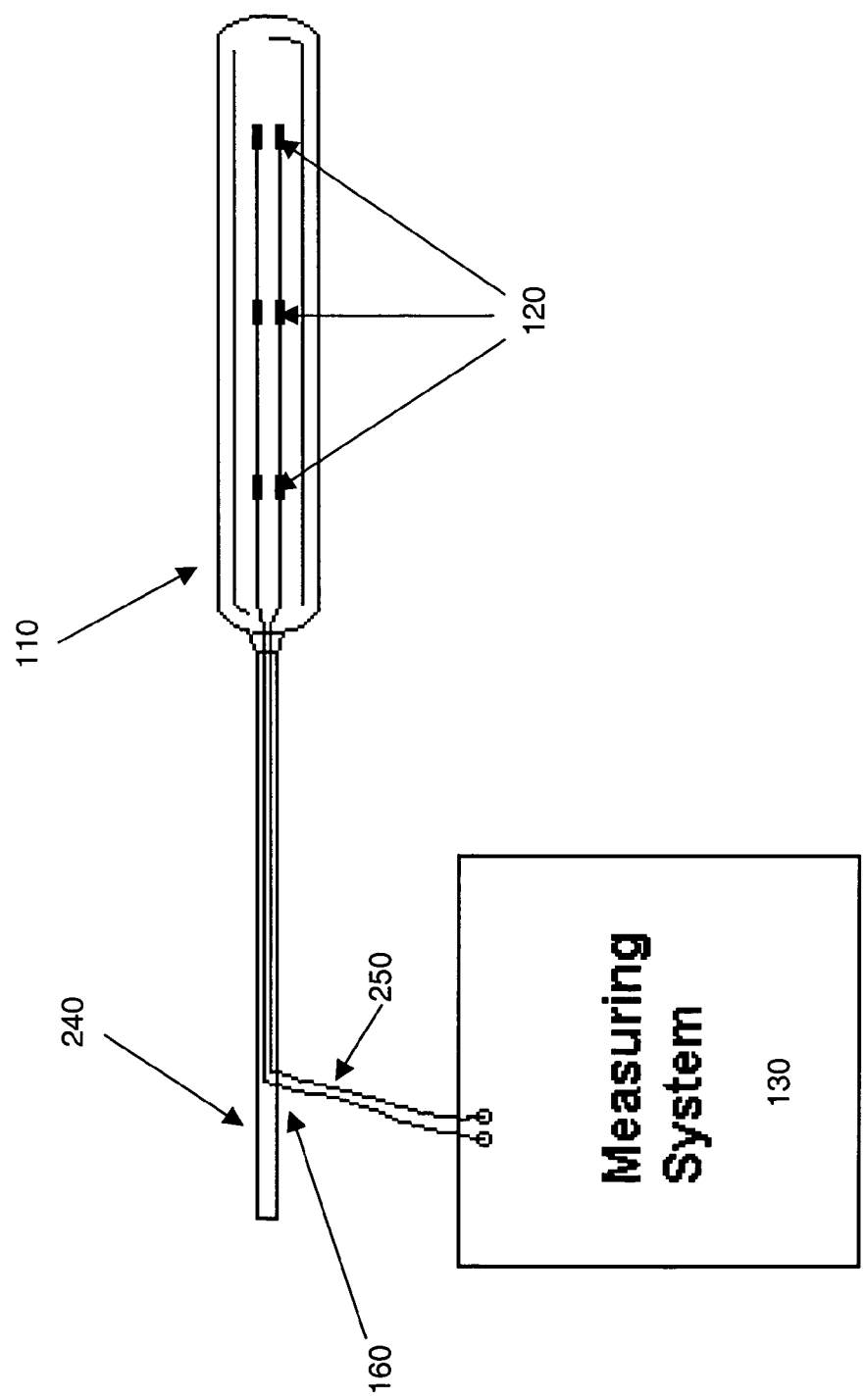
FIG. 5 depicts an embodiment of a physiological change monitoring system.

FIG. 5 depicts an embodiment of a flexible conduit 110 including sensors 120 distributed along the length of the flexible conduit and coupled to a measurement determining unit 130. Flexible conduit 110 may have a trough shaped cross section. A retracting conduit 240 may be coupled to flexible conduit 110. Sensors 120 each may be arranged in pairs of electrodes at least partially embedded in flexible conduit 110. In an embodiment, the number of sensors coupled to a flexible conduit may be selected to optimally detect impedance and/or leaks. Any array or positioning of one or more impedance sensors may be used in the flexible conduit. Each sensor may be coupled to wires 250 that also may be at least partially embedded in flexible conduit 110. Wires 250 may extend into retracting conduit 240. Wires 250 may be at least partially embedded in retracting conduit 240. In an embodiment, the wires 250 may exit a retracting conduit 240 near a proximal end 160 of the retracting conduit. Each wire 250 may be independently coupled to a measurement determining unit 130. In an embodiment, wires from sensors may be coupled together and the coupled wires may be connected to a measurement determining unit.

Figure 6B:
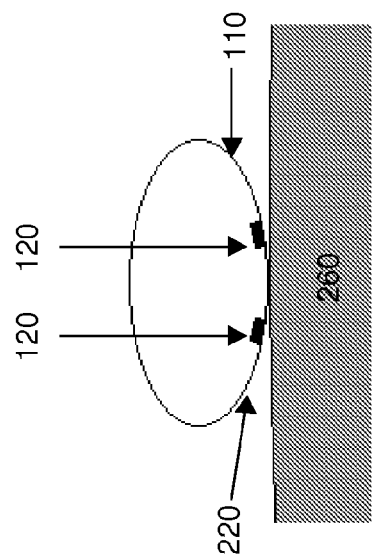
FIG. 6*b* depicts an embodiment of a flexible conduit with sensor that can directly contact a site.
Figure 6A:
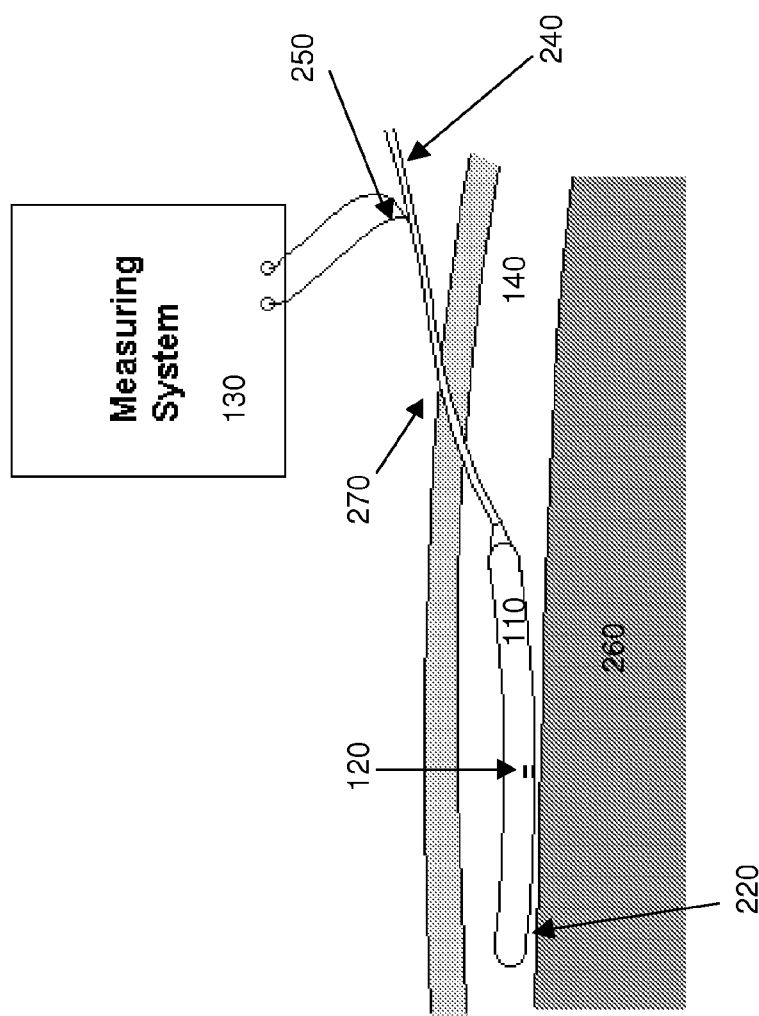
FIG. 6*a* depicts an embodiment of a flexible conduit with a cross-section that has a convex portion.

FIG. 6a is a depiction of a flexible conduit that has a convex or humped cross-section. The convex section 220 may be placed in direct contact with a target organ or site 260 to obtain impedance measurements. Flexible conduit 110 may be coupled to a separate retractor conduit 240. Retractor conduit 240 may be drawn through a puncture incision 270 in the skin and/or musculature of an involved body cavity or body space 140. Sensors 120 may be at least partially embedded in a flexible conduit 110. Sensors 120 may be coupled to wires 250 that are at least partially embedded in flexible conduit 110 and retractor conduit 240. Wires 250 may exit retractor conduit 240 at a point 270 outside of the skin of the patient where they may be appropriately connected to an impedance measuring unit 130. When flexible conduit 110 is positioned in a body, a sensor 120 may be positioned such that the sensors substantially directly contact the target organ or site 260. FIG. 6b depicts an embodiment of a flexible conduit 110 that includes sensors 120 that directly contact a target organ or site 260. The convex cross-sectional shape 220 of flexible conduit 110 facilitates contact of an exposed surface of sensors 120 with a surface of the target organ or site 260 to facilitate accurate impedance measurements.

In some embodiments, a portion of a cross-section of a flexible conduit may be convex. A convex portion of flexible conduit may be configured to enhance and stabilize direct contact of electrode surfaces of a sensor with a surface of a target organ, tissue, or site. Direct contact between sensors and a surface of a site may facilitate direct impedance measuring. Direct impedance measurements may be useful in clinical practice as an indirect measure of tissue edema. Tissue edema may occur in patients in different organs due a host of pathological processes. Edema of tissues or organs may cause a change in impedance due to an alteration of the ratio between electrically conductive and resistive elements within a tissue or organ. In an embodiment, a flexible conduit may be positioned in a body cavity in direct contact with a target organ, tissue, or site. Flexible conduit may be positioned during a surgical procedure or by any number of percutaneous procedures performed at the bedside of the patient, in an ICU setting, in a clinic, or in a minor procedure room.

In certain embodiments, a physiological change monitoring system may directly measure impedance and monitor physiological changes in a body. A physiological change monitoring system may be used: in the cranial vault to monitor brain edema; in the pleural space to monitor lung edema; in an extremity compartment to measure edema of the muscles or other tissues of the extremity; in the abdominal cavity to measure edema of the liver, bowel, pancreas, or other intraabdominal or retroperitoneal organs or tissues; in the pericardium to measure edema of the heart; in the retroorbital space to measure ocular edema; in the mediastinum to measure edema of mediastinal structures such as the esophagus; in the scrotum to measure testicular edema; in subcutaneous spaces or body cavities to measure edema of muscle or skin flaps after breast surgery or plastic surgery; or in combinations of these and other tissues or body cavities. Length and width of a flexible conduit of a physiological change monitoring system may be specifically configured for the specific body cavity the flexible conduit is intended to occupy. In an embodiment, a flexible catheter may be configured to be used in multiple areas of a body and/or in multiple body cavities.

In some embodiments, impedance measurements may be obtained intermittently as a means of surveillance against the development of organ edema and/or to measure the progression and/or resolution of some pathologic process causing organ edema over extended periods of time. Impedance measurements may be obtained continuously to measure the short-term effect of different physiologic processes on the development of organ edema. Baseline impedance values for a specific target organ or tissue in a specific patient may be compared to subsequently obtained values as a means of assessing the development or resolution of edema. In an embodiment, standard values for impedance obtained from specific organs or tissues in healthy individuals may be compared to values obtained from the same organ or tissue in a given patient.

Figure 7:
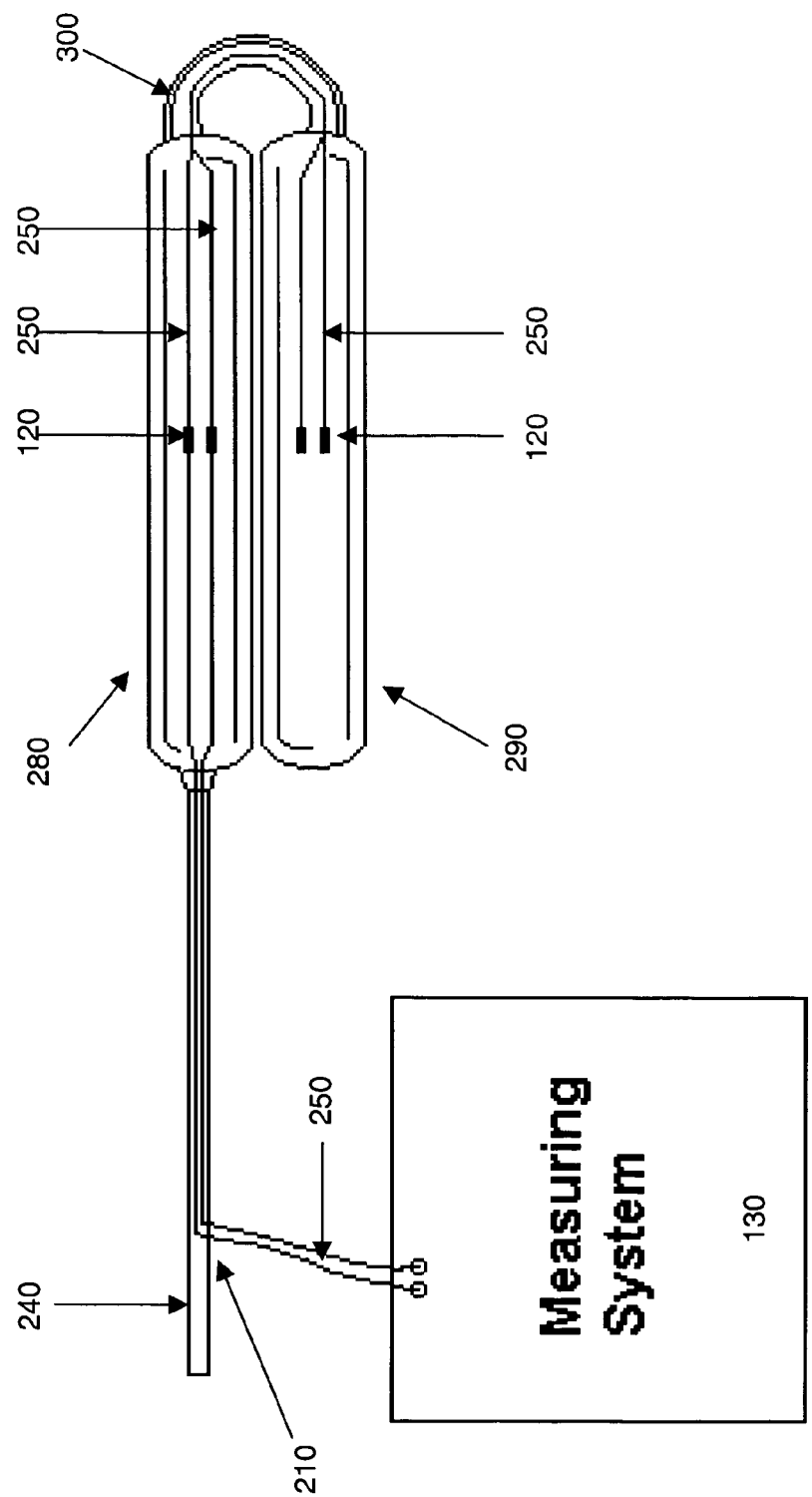
FIG. 7 depicts an embodiment of a physiological change monitoring system.

FIG. 7 depicts an embodiment of a system for determining impedance in a body cavity or part. The system may include more than one flexible conduit. In some embodiments, a first flexible conduit 280 and a second flexible conduit 290 may be coupled by one or more connector conduit 300. Additional flexible conduits may also be added in the same manner by additional connector conduits. Several flexible conduits may be coupled by a plurality of connector conduits. One of the flexible conduits may be configured to be coupled to a retractor conduit that exits the patient through an opening in the body. In some embodiments, the more than one flexible conduits, connector conduits, and retractor conduits may be a single piece. In an embodiment, two flexible conduits containing sensors are coupled in a tandem configuration to increase the surface area of the leak-detecting components.

First flexible conduit 280 and second flexible conduit 290 may have similar or different cross-sectional shapes. Each flexible conduit may include one or more sensors 120. Sensors may be at least partially embedded in a flexible conduit. In FIG. 7, one sensor pair 120 may be positioned in first flexible conduit 280 and one sensor pair 120 may be positioned in second flexible conduit 290. Each sensor may be coupled to separate wires 250 that are completely or partially embedded in flexible conduits 280, 290. Wire 250 may extend from sensor 120 through second flexible conduit 290, a connecting conduit 300, a first flexible conduit 280, and a retracting conduit 240. Wire 250 may exit physiological change monitoring system at a point 210 on retracting conduit 240. In an embodiment, wires may exit retracting conduit 240 at an end. Wires 250 may be coupled to a measurement determining unit 130, such as an impedance monitoring unit. An impedance measuring unit and a sensor may use various impedance measuring methods known in the art, including but not limited to impedance determining methods using high frequency modulated currents or current pulses and/or methods using various test current pulses. In certain embodiments, a connecting conduit may include a malleable material to promote retention of the tandem configuration after surgical placement. Malleable materials include metal wires and/or malleable, inelastic polymers. Connecting conduit may be formed of a material similar to the flexible conduit and/or a malleable material. In an embodiment, a malleable material is embedded in a pliable material such as latex, silicone, plastic and/or other similar materials. Inclusion of a malleable material in a connecting conduit may allow the connecting conduit to be bent and/or manipulated into a desired shape. Malleable material may cause a connecting conduit to remain in the desired shape during use.

At the time of surgery, an operator may bend and/or manipulate the connector conduit to arrange the flexible conduits side-by-side, end-to-end, or in any other configuration. An operator then may position the flexible conduits behind an area of anastomosis such that flexible conduits at least partially circumscribe the anastomosis. In an embodiment, a U-shaped flexible conduit may be used such that trough-shape of each flexible conduit is cupped around the tissues of a gastrointestinal tract such that the flexible conduit at least partially surrounds the anastomosis. This configuration may increase the number of sensors proximate an anastomosis. This configuration may also allow the pooling of leaking fluids into the channel of the flexible conduit and may increase the effective surface area of a flexible conduit. This configuration may enhance the detection, quantification, and localization of anastomotic leaks. This configuration may preserve facilitation of manual removal of the flexible conduit and may reduce the likelihood of additional surgery for removal of the flexible conduit.

In certain embodiments, a physiological change monitoring system may provide a method of leak detection, quantification, and localization by providing an impedance signal correlated to a physical state of the gastrointestinal tract where gastrointestinal contents leak into the tissues or body cavities surrounding the gastrointestinal tract. A physiological change monitoring system may detect and quantify gastrointestinal leaks from any portion of the gastrointestinal system including, but not limited to, the esophagus, the stomach, the small intestine, the liver, the pancreas, the large intestine and the rectum.

At the time of surgery, a flexible conduit of a physiological change monitoring system may be placed in a body cavity proximate a gastrointestinal anastomosis. A physiological change monitoring system may remain in position for several weeks post-operatively. When desired, an operator may remove a physiological change monitoring system manually without necessitating a further operation for removal. By positioning a flexible conduit in proximity to a gastrointestinal anastomosis, sensors on the flexible conduit have a greater likelihood of detecting an anastomotic leak by virtue of having a higher likelihood of coming into contact with leaks from the anastomosis, including leaking contrast solution.

Figure 8:
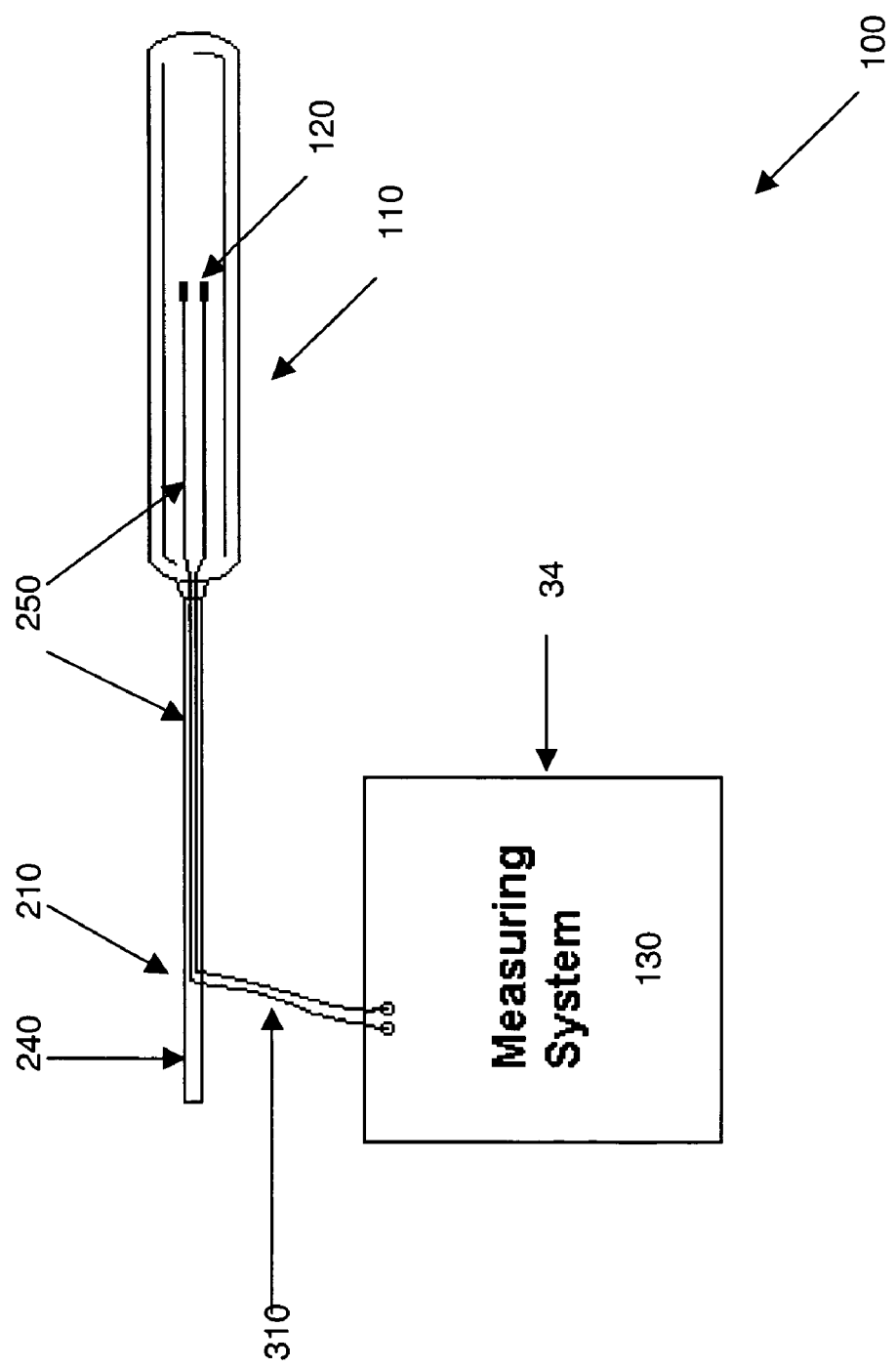
FIG. 8 depicts an embodiment of a physiological change monitoring system.

FIG. 8 depicts an embodiment of system for determining physiological changes in a body. In some embodiments, a physiological change monitoring system may include flexible conduit 110 and retractor conduit 240 coupled together. Flexible conduit 110 and retractor conduit 240 may be a single unit. Wires 250 connect sensors 120 in flexible conduit 110 to a measurement determining unit 130. Wires 250 connected to sensors 120 may be completely embedded in flexible conduit 110 and retractor conduit 240. At least partially embedding wires in flexible conduit and/or retractor conduit may insulate the wires. Retractor conduit 240 is configured such that free ends of the wires 310 exit retractor conduit 240 at a point 210 near an end of retractor conduit proximate to a user. Free ends of the wires 310 are configured to be coupled to a measurement determining unit 130. Free ends of the wires 310 may be coupled to measurement determining unit 130 to obtain measured impedance values during use.

Figure 9:
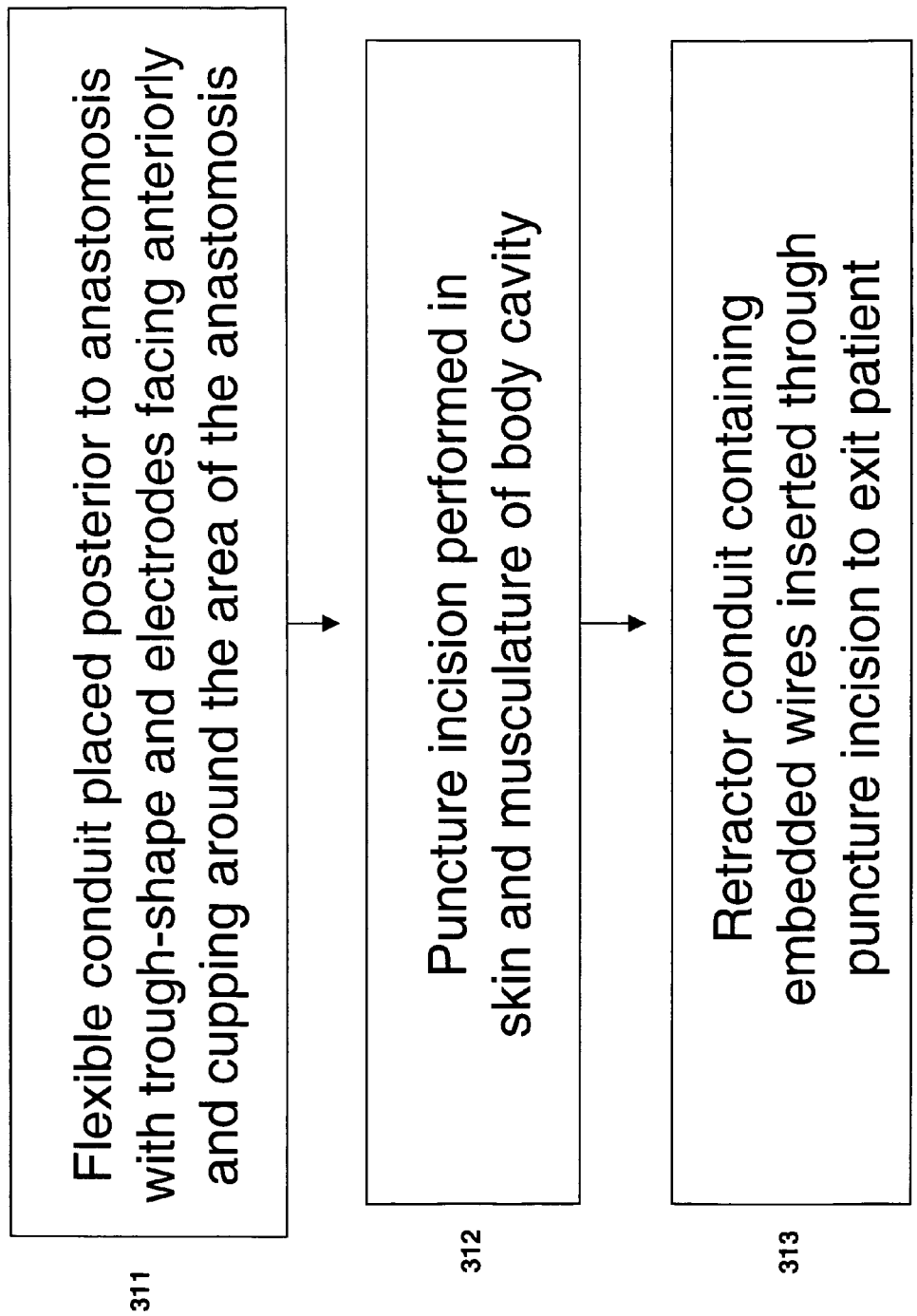
FIG. 9 depicts a process flow diagram of an embodiment of the steps performed at the time of surgery by the user to position a physiological change monitoring system.

FIG. 9 depicts a process flow diagram of an embodiment of the steps performed at the time of surgery by the user to position a physiological change monitoring system. After the gastrointestinal anastomosis has been created and while the incision is still open, a flexible conduit may be placed manually or via surgical instruments (e.g., laparoscopic or thoracoscopic instruments) by the user behind the anastomosis 311. A flexible conduit is positioned with the trough shape of a flexible conduit and a surface of sensors facing anteriorly toward the anastomosis, so that the flexible conduit is cupped around the tissues of the body part surrounding the anastomosis 311. Next, a stab or puncture incision may be created through the skin and musculature surrounding the body cavity proximate to the anastomosis and leak-detecting catheter 312. Retractor conduit containing wires attached to sensors may be then inserted or passed through the puncture incision so that an end of the retractor conduit exits the body along with the free ends of the wires attached to the sensors 313.

Figures 10A, 10B:
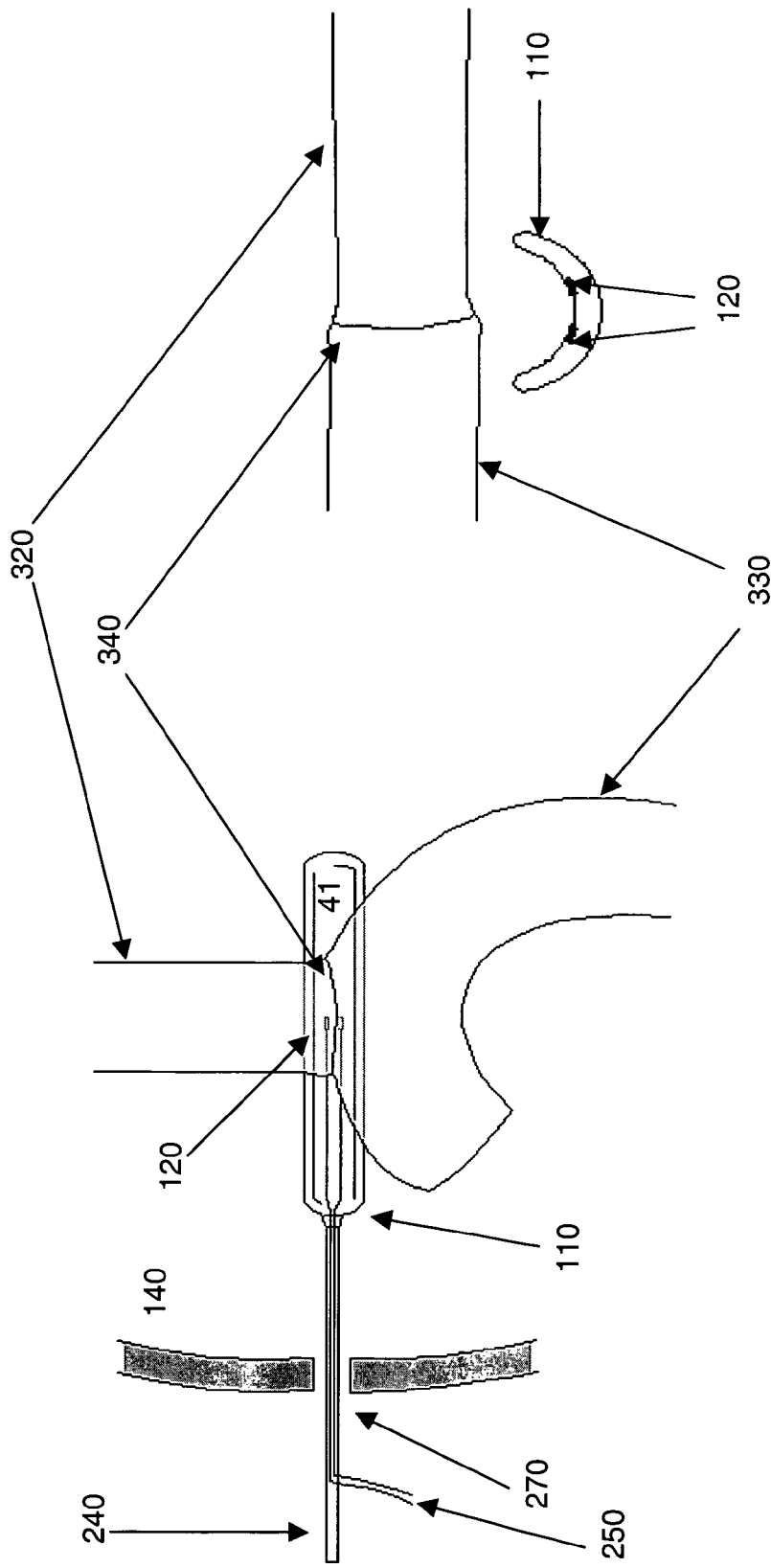
FIG. 10a depicts an embodiment of a physiological change monitoring system positioned proximate an upper gastrointestinal anastomosis.
FIG. 10b depicts an embodiment of a side view of an upper gastrointestinal anastomosis.

FIG. 10a depicts an embodiment of a physiological change monitoring system positioned proximate an upper gastrointestinal anastomosis. A segment of esophagus 320 and a segment of small bowel 330 may be surgically joined together to form an upper gastrointestinal anastomosis 340. Flexible conduit 110 of a physiological change monitoring system may be positioned behind the anastomosis 340, relative to the user, such that sensors 120 of the physiological change monitoring system are positioned directly behind the circumference of the anastomosis. Retractor conduit 240 may extend away from the area of the anastomosis. Retractor conduit 240 may include wires 250 coupled to the sensors. In an embodiment, retractor conduit 240 passes through a puncture incision 270 in the skin and musculature of the body cavity 140 and the ends of wires 250 exit the retractor conduit outside the body. FIG. 10b depicts an embodiment of a side view of an upper gastrointestinal anastomosis 340 that surgically joins a segment of esophagus 320 and the small bowel 330 together. A cross-sectional view of flexible conduit 110 and sensors 120 illustrates the posterior position of the flexible conduit 110 with respect to the anastomosis 340. Surfaces of sensors 120 of a flexible conduit may also be positioned anteriorly. Edges of the trough-like flexible conduit 110 may be directed anteriorly and contact or be proximate to the tissues of the gastrointestinal tract surrounding the anastomosis 340.

Figure 11:
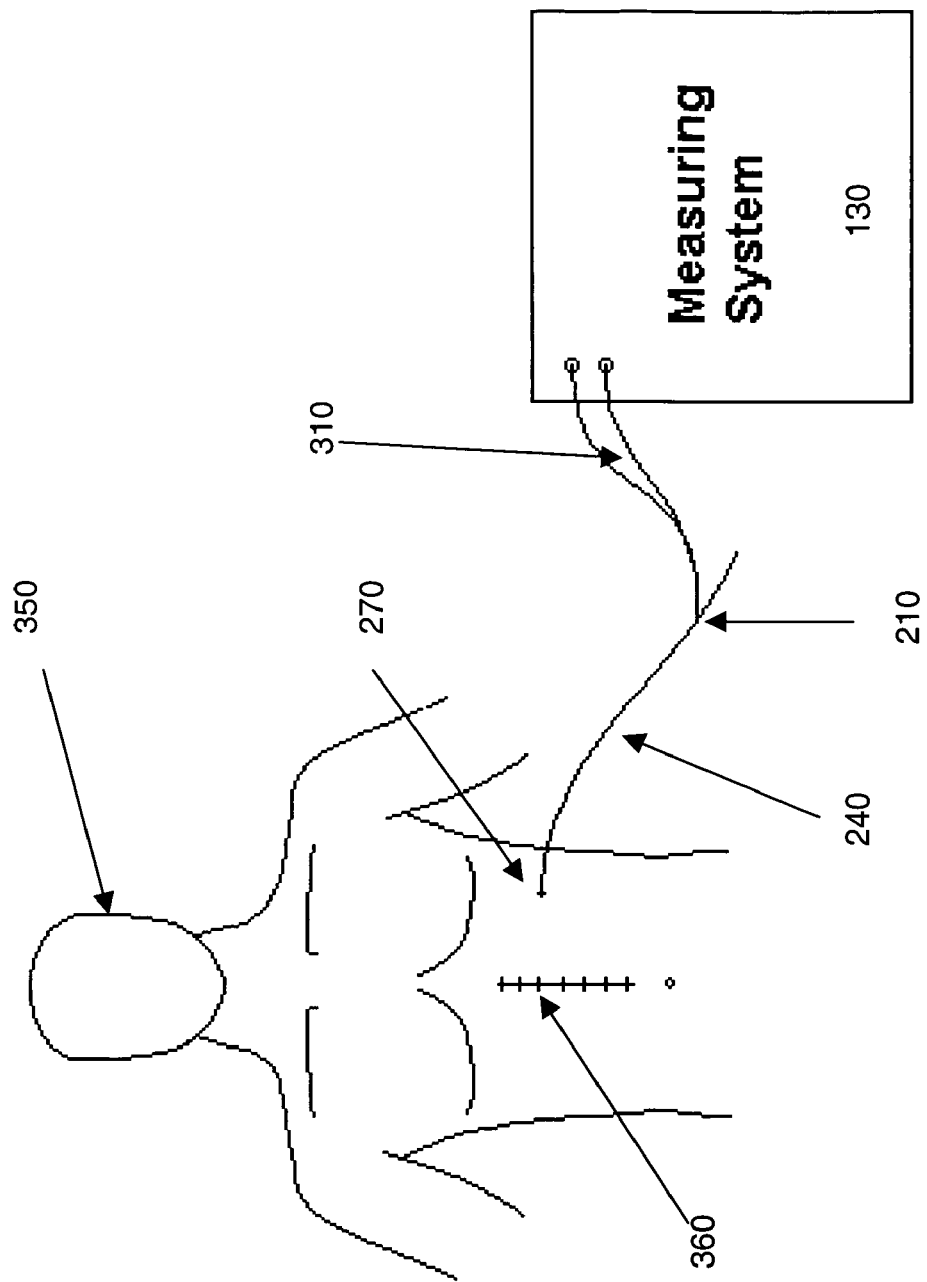
FIG. 11 depicts an external view of an embodiment of a physiological change monitoring system in a patient.

FIG. 11 depicts an external view of an embodiment of a physiological change monitoring system in a patient. A patient 350 may have an abdominal operative incision 360. A separate puncture incision 270 may be established through the skin and musculature of the abdominal wall to allow passage of retractor conduit 240 of a physiological change monitoring system. Free ends of the wires 310, which are coupled to the sensors, exit at a point 210 on a retractor conduit 240 and may be connected to a measurement determining unit 130 external to the patient 350.

Figure 12:
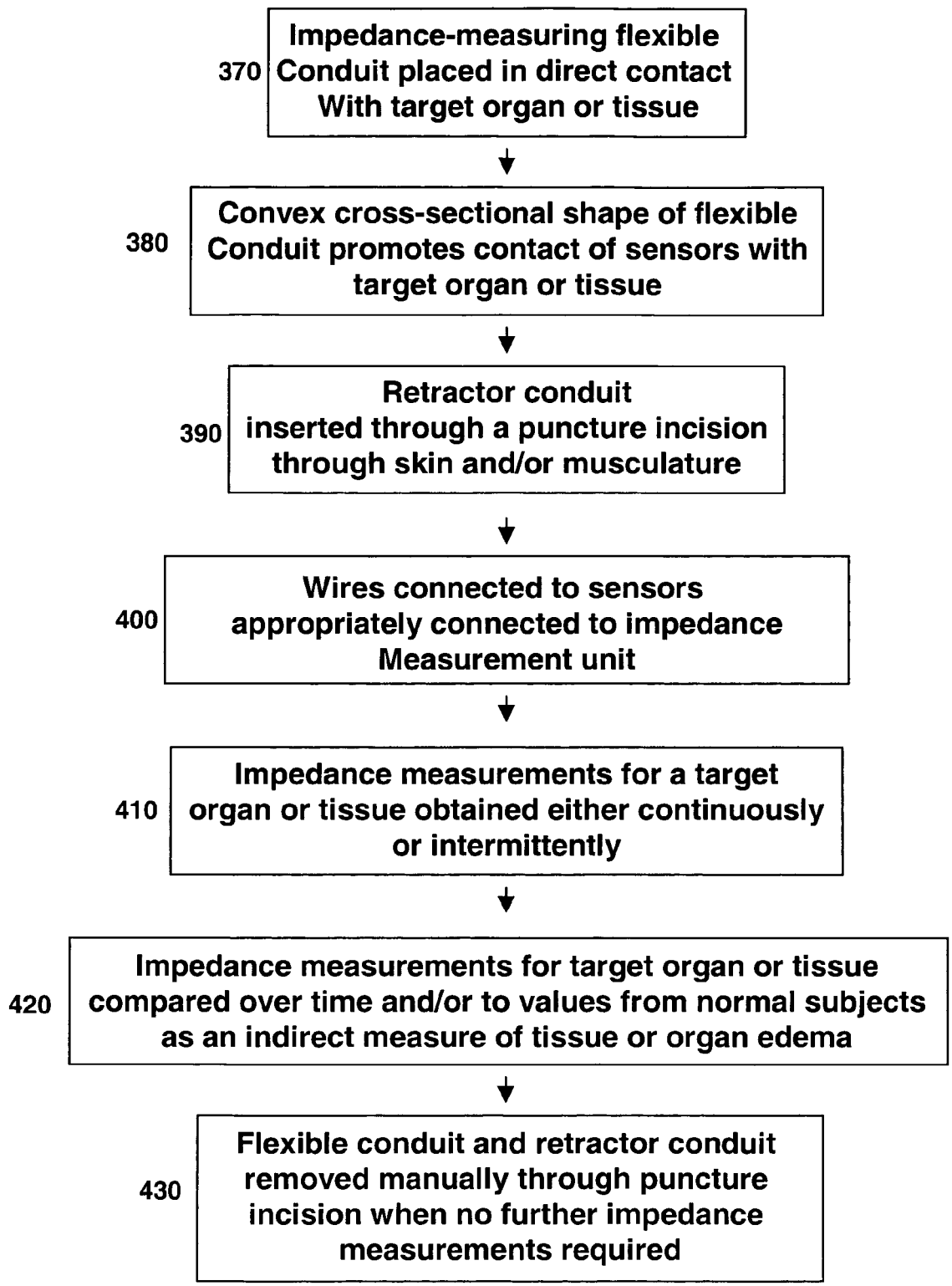
FIG. 12 depicts a process flow diagram of an embodiment of a method of positioning a physiological change monitoring system.

FIG. 12 depicts a process flow diagram of an embodiment of a method of positioning a physiological change monitoring system such that the sensors are in contact with a target organ or site and directly monitoring impedance of the target organ or site. A flexible conduit of a physiological change monitoring system may be positioned in direct contact with a site either at the time of surgery (either in conjunction with open operations or minimally invasive operations such as laparoscopic or thoracoscopic operations) or through various percutaneous methods that can be performed under sterile conditions at the bedside of the patient, in an intensive care unit, or in a minor procedure room 370. The convex or humped cross-sectional shape of a flexible conduit may be positioned to facilitate direct contact between the exposed surface of sensors and a surface of the site 380. A retractor conduit may be inserted through a puncture incision in the skin and/or musculature of the involved body space or cavity such that at least a portion of the retractor conduit is external to the patient 390. Wires coupled at an end to sensors may be connected to a measurement determining unit 400. Wires may be positioned at least partially in the retractor conduit. A physiological change monitoring system may obtain direct impedance measurements for a site either intermittently or continuously 410. Impedance measurements obtained from the site may be compared to other impedance measurements obtained over time and/or to established normal values for the site 420.

Normal values for a site may be obtained from normal subjects to detect changes in the impedance of the target organ or site. Changes in impedance may be an indirect indication of organ or tissue edema due to pathological processes. When no further impedance measurements in the site are required, the physiological change monitoring system may be removed by manually withdrawing the retractor conduit and the coupled flexible conduit through a previously created puncture incision 430. In an embodiment, surgery may not be required to remove the physiological change monitoring system.

In some embodiments, contrast solution may be used with a physiological change monitoring system to detect the presence of leaks within a body. A contrast solution may be ingested by a patient, injected into a patient, and/or otherwise delivered to a patient (e.g., via enterally placed tubes that are commonly used in surgical practice). If a leak is present in the body, contrast solution may flow from the leak. Contrast solution may flow into a flexible conduit of a physiological change monitoring system. In an embodiment, contrast solution may flow through a channel of a flexible conduit. A physiological change monitoring system may detect leaking contrast solution by a change in impedance at the site.

In certain embodiments, contrast solution may be a salt contrast solution composed of a salt dissolved in water. The salt may be sodium chloride. A salt contrast solution may contain a higher concentration of sodium chloride than bodily fluids. A salt contrast solution may be configured to posses a lower measured impedance than normal bodily fluids. Sensors may be configured to differentiate a salt contrast solution from normal bodily fluids that surround the gastrointestinal tract in a patient who has undergone a gastrointestinal anastomosis. In an embodiment, the concentration of sodium chloride may be established by a pre-determined molarity, molality, osmolarity, osmolality, or predetermined measured impedance value of the salt contrast solution. The pH of the salt contrast solution may be adjusted as needed. A salt contrast solution may be sterilized. A salt contrast solution may be used in a non-sterilized form.

In some embodiments, contrast solution may be administered to a patient such that it accumulates in a region of the upper gastrointestinal tract possessing a gastrointestinal anastomosis. Patients may swallow the contrast solution. Contrast solution may be delivered to the patient via enterally placed tubes. Contrast solution in the gastrointestinal tract proximate an anastomosis may leak from the gastrointestinal tract and into surrounding tissues or body cavities where the contrast solution may be detected by sensors of the physiological change monitoring system.

In some embodiments, impedance measurements may be obtained in conjunction with the administration of a contrast solution into a portion of the gastrointestinal tract that contains a gastrointestinal anastomosis. Prior to the administration of contrast solution, a patient may be placed into the supine position so that a flexible conduit, positioned behind the anastomosis, relative to the user at the time of surgery, may collect fluid flowing in a downward direction from the site of the leak. Impedance measurements may be initiated prior to administration of the contrast solution in order to obtain a baseline impedance measurement. Impedance measurement may continue while the patient either ingests a contrast solution or a contrast solution is otherwise delivered into the gastrointestinal tract.

For a pre-determined period of time after ingestion of a contrast solution, impedance may be measured and displayed. The impedance may be displayed as a two-dimensional graph with the ordinate representing impedance values and the abscissa representing time units to obtain a curve of impedance over time. In some embodiments, the impedance may be processed, analyzed, and displayed by a computer. Contrast solution may be configured to have a lower measured impedance than normal bodily fluids. Contrast solution leaking from a site that comes in contact with a sensor may cause the impedance measuring unit to measure an impedance value less than the baseline value, confirming the presence of a leak. Furthermore, the degree of a leak may be quantified by obtaining an integral of the impedance curve over the pre-determined time interval, as expressed by the following equation:

$$Q = \int_0^x (Z_B - Z_t) dt \quad \text{(Equation 1)}$$

where,
Q, is the quantified leak value;
$Z_B$, is the baseline impedance value; and
$Z_t$, is the impedance value at any given time, t, over the time interval, 0 to x time units.

Contrast solutions may include solutes other than sodium chloride and/or solvents other than water. A contrast solution may be configured such that the solution absorbs a specific wavelength of light. Measurement determining unit may analyze the amount of absorbed light to determine if a leak is present. In an embodiment, the solute is a biologically inactive compound. Solutes in a contrast solution may include, but are not limited to: dissolved ions, such as fluoride, bromide, carbonate, bicarbonate, hydroxide, potassium, cupric ion, lead ion, silver ion, gold ion, sulfide, nitrate, ammonium, iodide, hydrogen ion or hydronium ion, calcium, anionic surfactants, organic salts or bases or acids, or others; dissolved gases such as oxygen, carbon-dioxide, helium, chlorine, or others; non-ionic dissolved metals or metals in a liquid suspension such as silver, gold, lead, iron, or others; organic molecules such as nucleic acids, proteins, lipids or liposomes, or heme-group-bearing macromolecules, or others; solutes containing radioisotopes; dissolved polymers such as polyethylene glycol, soluble silicones, or others; or mixtures thereof. Solvents in a contrast solution may include, but are not limited to: glycerin; oils; liquid silicones; or polar solvents such as ethanol; ammonia; iodine; methanol; isopropyl alcohol; dimethyl sulfoxide; dimethylformamide; ethylene glycol; propylene glycol; dioxane; THF; any solvent or solvent/solute combination set to a pre-determined temperature; or others.

In some embodiments, one or more sensors may detect a value other than impedance. In an embodiment, a physiological change monitoring system may include sensors that measure impedance and sensors that measure other values. Sensors in a physiological change monitoring system may include, but are not limited to: ion-selective field effect transistors; molecularly-imprinted-polymer-biosensors; photodetectors; temperature-detecting thermisters; detectors of radioactivity; or piezoelectric-crystal transmitter/receiver units. Sensors may be connected to a measurement determining unit or measurement determining unit corresponding to the type of sensor used. A single physiological change monitoring system may be connected to several different devices capable of measuring impedance and/or other values. Different measuring devices may be housed in a single measurement determining unit to facilitate operation of the system.

In some embodiments, a physiological change monitoring system may monitor pH. Monitoring pH may be useful after vascular operations, after gastrointestinal or abdominal operations, in and around the lungs in the setting of various pathological or post-surgical processes, organ transplantation, after cardiac surgery, bypasses, hip operations, and crush injuries to legs. When blood does not flow to a body site, the pH of the fluid around the site drops. The pH of the fluid around the site may be monitored by a flexible conduit at the site, which may detect pH changes in the site.

In some embodiments, a physiological change monitoring system may be used in the lungs. After lung surgery, too much fluid may develop around the lungs. Often a drain may be used to remove fluid from around the lungs. Rather than using a drain, a physiological change monitoring system may be used. Flexible conduit of a physiological change monitoring system may be configured to allow fluid to flow away from the lungs. In an embodiment, a channel in a flexible conduit may be used to direct the flow of fluid. Additionally, fluid developing around the lungs may cause a detectable change in pH. Sensors of a physiological change monitoring system may monitor changes in pH around the lungs, and thus monitor the amount of fluid building up in the lungs.

A physiological change monitoring system may also be used to detect air leaks in the lungs. In some embodiments, air leaking from the lungs may cause a change in impedance. Sensors of a physiological change monitoring system may be configured to detect the change in impedance corresponding to leaking air. In certain embodiments, a contrast gas that is either not present or not present in large quantities in the body may be used in a similar method to contrast solutions with a physiological change monitoring system. A contrast gas may be any gas. A contrast gas may be administered to the patient or inhaled by the patient. If a leak is present in the lungs, the contrast gas may flow from the leak. A physiological change monitoring system positioned proximate the lungs may detect the leaking contrast gas. In certain embodiments, the sensors in the physiological change monitoring system may be ion detectors, impedance detectors, and/or any other sensors.

Since the types of measured values obtained by the measuring device depend on the type of sensor and contrast solution being used, in some cases the measured value obtained at baseline may be smaller in magnitude than the measured values obtained when the sensor detects leakage of the contrast solution. When a value other than impedance is monitored, the quantified leak value, Q, may be the integral of the absolute value of the difference between the measured value at baseline, $V_B$, and the measured value, $V_t$, at any time, t, is obtained over the interval, 0 to x time units, as expressed by the following equation:

$$Q = \int_0^x (|V_B - V_t|) dt \qquad \text{(Equation 2)}$$

In some embodiments, more than one sensor may be distributed along a length of a flexible conduit. Each sensor may include a pair of electrodes coupled to a flexible conduit. Each sensor and/or electrode may be associated with a single wire separate from the wires of other sensors. In some embodiments, a wire configured to connect a sensor to a measurement determining unit may be at least partially embedded in flexible conduit and/or retractor conduit. Inclusion of multiple sensors along a length of a flexible conduit may facilitate identification of the location of a leak. Including multiple sensors in a flexible conduit may improve leak quantification analysis.

In certain embodiments, a multiple sensor flexible conduit may be used in conjunction with delivery and/or ingestion of a contrast solution by a patient. Impedance curves may be generated as previously described for each sensor simultaneously and differential impedance curves generated by each sensor may identify the location of a leak. In an embodiment, one or more sensors may detect a change in impedance after the administration of salt contrast solution while one or more sensors may not register a change. Sensors registering a change in impedance may be the sensors closest to a leak.

In an embodiment, all sensors in a flexible conduit may detect a change in impedance, but one or more sensors may detect the change in impedance before other sensors. The time at which a sensor detects a change in impedance after the administration of salt contrast solution may be obtained by examining the impedance curve generated by an impedance measuring unit. The time a sensor detects an initial change in impedance may be identified by from the impedance curve. The time of initial change is $t_i$. A value for $t_i$ may be generated for each sensor. The sensor associated with the smallest value for $t_i$ may be the sensor closest to the area of a leak. Additionally, values for a quantified leak value, Q, may be obtained for each sensor and compared to one another. Larger values for Q may indicate that a sensor is proximate the area of a leak.

Figure 13:
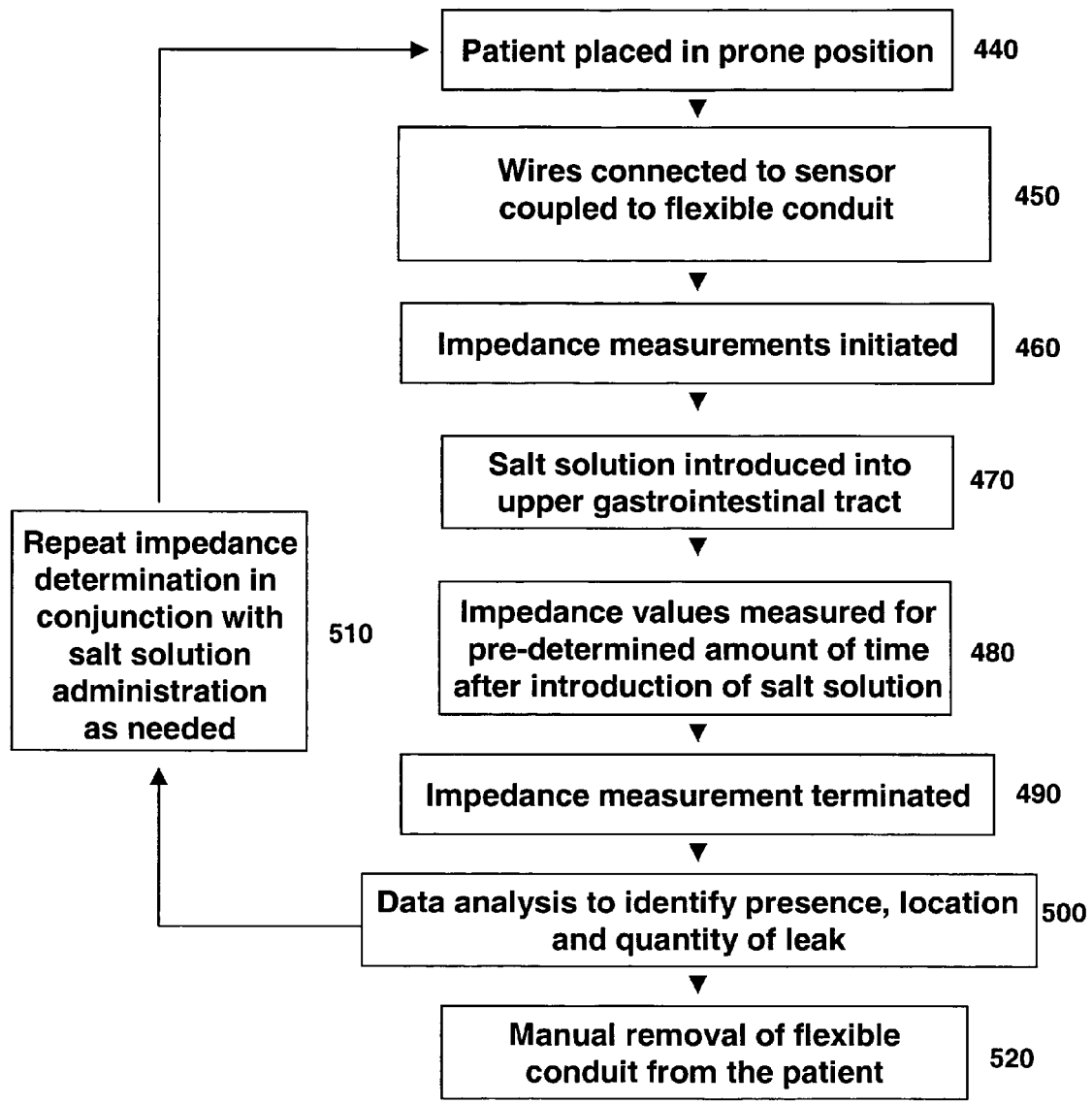
FIG. 13 depicts a process flow diagram of an embodiment of a method of obtaining impedance measurements from a physiological change monitoring system.

FIG. 13 depicts a process flow diagram of an embodiment of a method of obtaining impedance measurements from a physiological change monitoring system. A patient with a physiological change monitoring system may be placed in a supine position 440. A physiological change monitoring system may be positioned in the patient as previously described. A flexible conduit may be positioned behind the anastomosis at the time of surgery. Wires connected to the sensors may be coupled to the impedance measuring unit to generate values for impedance and/or other measured values, such as oxygen concentrations 450. Next, impedance measurements may be initiated 460. A contrast solution may be introduced into a region of the gastrointestinal tract containing a gastrointestinal anastomosis 470. Contrast solution may be delivered to a patient or a patient may ingest contrast solution. Then impedance may be measured during introduction of the contrast solution into the gastrointestinal tract and after introduction of the contrast solution for a pre-determined period of time 480. After a predetermined time period, the measurement of impedance values may cease 490. Data obtained during impedance measurement may be analyzed to identify the presence, location, and quantity of any existing gastrointestinal leak 500. Determining impedance values in conjunction with introduction of a salt contrast solution into the gastrointestinal tract may be repeated as necessary according to the clinical status of a patient 510. When the physiological change monitoring system is no longer necessary due to a decreased likelihood of leak formation, the physiological change monitoring system may be removed 520. Additional surgery may not be necessary to remove the physiological change monitoring system.

Figure 14B:
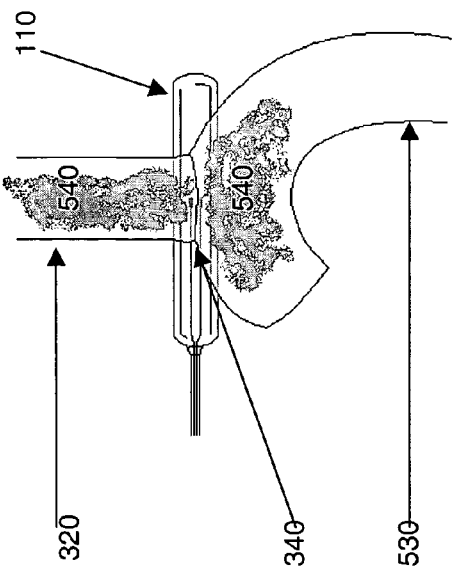
FIG. 14b depicts an embodiment of detecting gastrointestinal leaks in the area of an upper gastrointestinal anastomosis.
Figure 14D:
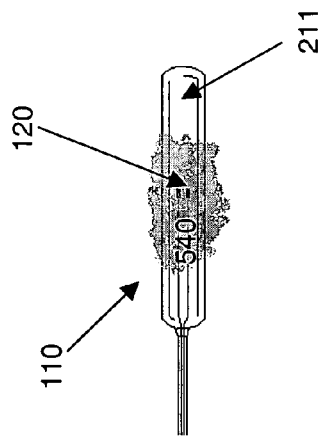
FIG. 14d depicts an embodiment a flexible conduit that detects gastrointestinal leaks in the area of an upper gastrointestinal anastomosis.
Figure 14A:
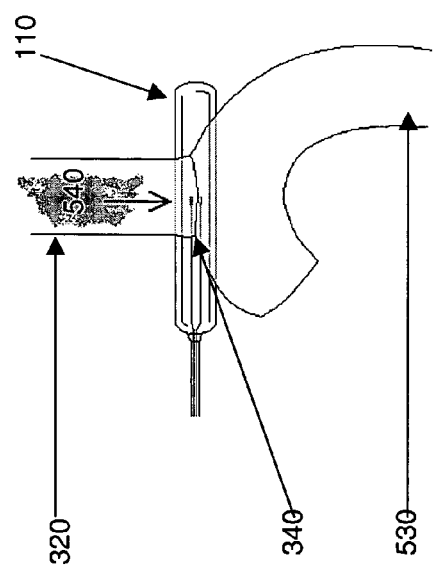
FIG. 14a depicts an embodiment of detecting gastrointestinal leaks in the area of an upper gastrointestinal anastomosis.
Figure 14C:
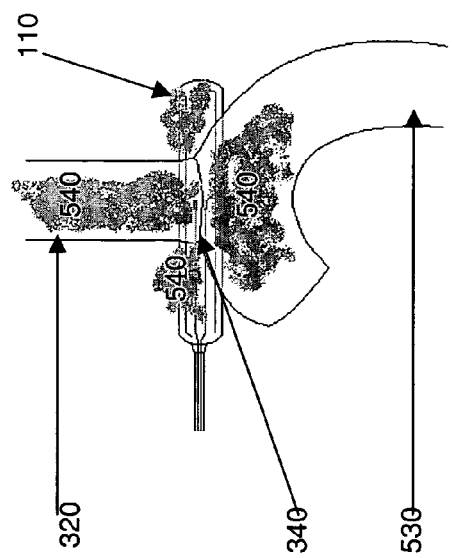
FIG. 14c depicts an embodiment of detecting gastrointestinal leaks in the area of an upper gastrointestinal anastomosis.

FIGS. 14*a-d* depict embodiments of detecting gastrointestinal leaks in the area of an upper gastrointestinal anastomosis. In FIGS. 14*a-d*, a segment of esophagus 320 may be surgically connected to a segment of small intestine 530 to establish an upper gastrointestinal anastomosis 340. A flexible conduit 110 may be positioned in the body cavity. In FIG. 14*a*, contrast solution 540 may be introduced into the gastrointestinal tract. In an embodiment, a patient swallows the contrast solution. Contrast solution may be administered by other appropriate routes such as via a naso-enteral tube. In FIG. 14*b*, contrast solution 540 administered into the gastrointestinal tract may pass to and accumulate in an area of the gastrointestinal tract possessing an anastomosis 340. In FIG. 14*c*, a leak in the gastrointestinal anastomosis 340 may allow contrast solution 540 to flow outside the gastrointestinal tract and over the area of the trough-shape of flexible conduit 110. In FIG. 14d, the esophagus and small bowel have been removed from the illustration for ease of visualization. Contrast solution 540 outside the gastrointestinal tract may flow due to gravity into a channel 211 of flexible conduit 110 and may contact sensors 120, which may be at least partially embedded in channel 211 of flexible conduit 110. In FIG. 14d, contrast solution 540 outside the gastrointestinal tract that contacts sensors 120 may cause a change in the measured impedance registered by the impedance measurement unit.

Figure 15:
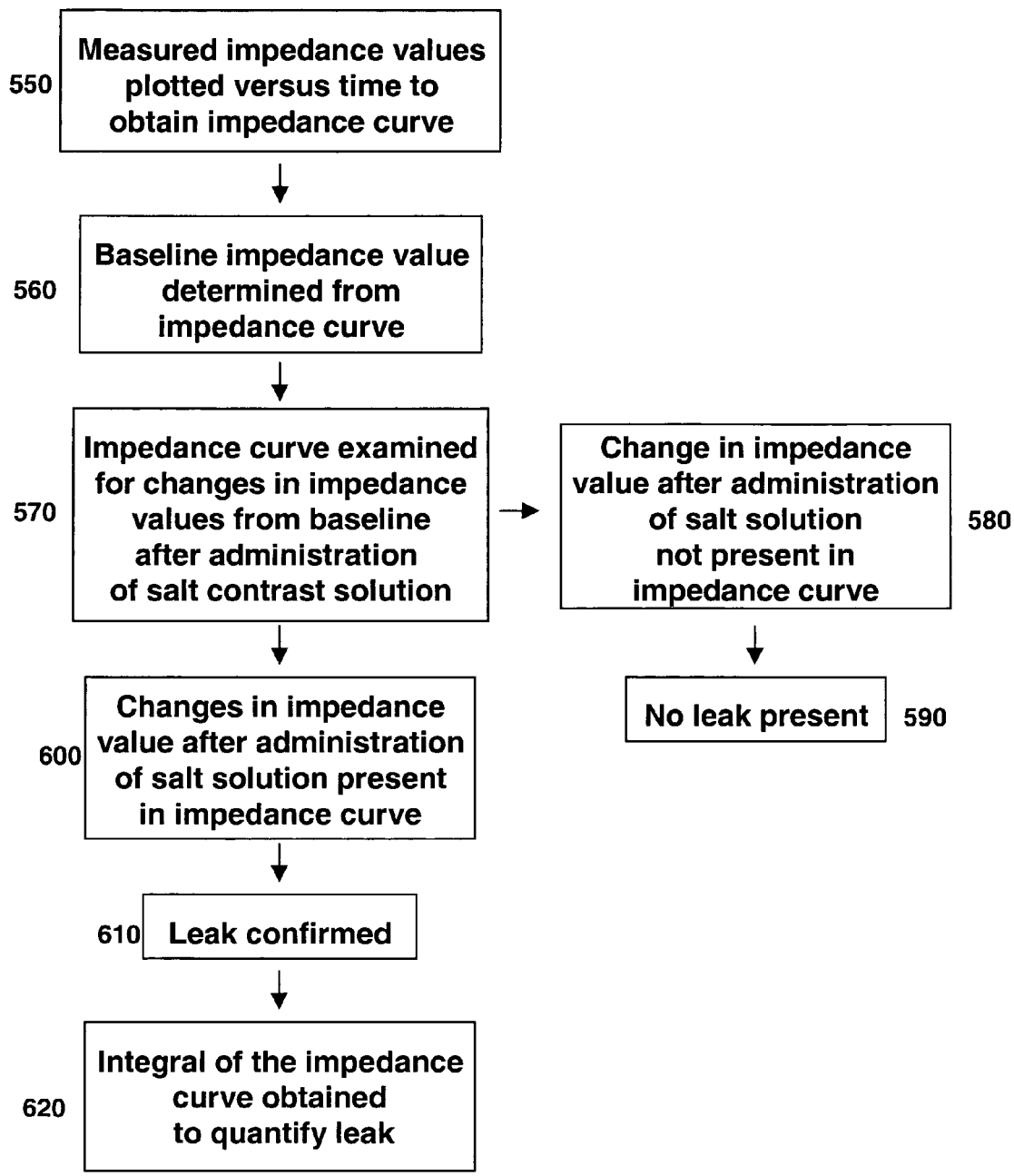
FIG. 15 depicts a process flow diagram of an embodiment of a method of analyzing data obtained by a physiological change monitoring system to identify the presence of a leak and quantify the leak.

FIG. 15 depicts a process flow diagram of an embodiment of a method of analyzing data obtained by a physiological change monitoring system to identify the presence of a leak and quantify the leak. Impedance values obtained by the leak-detecting catheter and measured by the impedance-determining device over the pre-determined time period may be plotted versus time to obtain an impedance curve 550. The impedance value observed from the region of the impedance curve corresponding to the initiation of impedance measurements prior to the administration of a salt solution may be the baseline impedance value 560. The region of the impedance curve corresponding to the period of time during and after which the salt contrast solution is administered to the patient may be analyzed for changes in impedance values compared to the baseline impedance value 570. When impedance values do not appear to change from the baseline impedance value after administration of salt solution 580, it may be concluded that a gastrointestinal leak is not present 590. When impedance values appear to change from the baseline impedance value after administration of salt solution to the patient 600, it may be concluded that a gastrointestinal leak is present 610. A confirmed gastrointestinal leak may be quantified by obtaining an integral of the impedance curve using Equation 1 or Equation 2, as previously described 620.

Figure 16B:
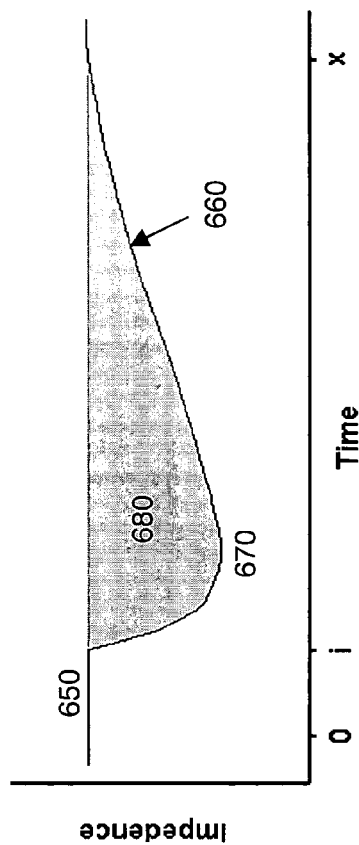
FIG. 16b depicts a schematic plot of an embodiment of an impedance curve obtained from a patient with a gastrointestinal leak
Figure 16A:
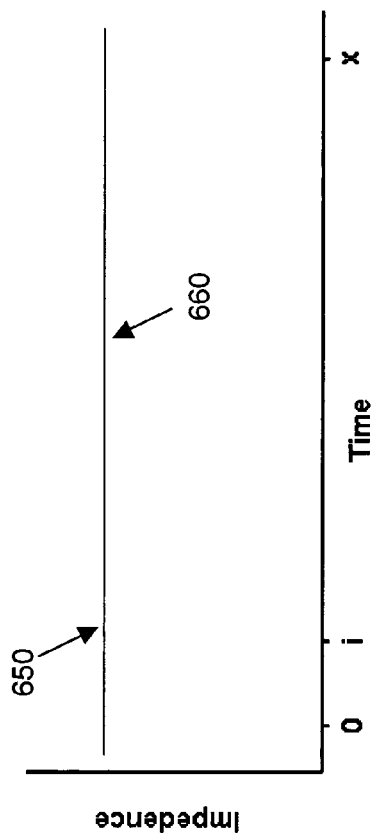
FIG. 16a depicts a schematic plot of an embodiment of an impedance curve obtained from a patient in whom a gastrointestinal leak is not present.

FIGS. 16a-b depict schematic plots of impedance curves obtained by plotting impedance values obtained by an embodiment of a physiological change monitoring system over a pre-determined time. In FIGS. 16a-b, the ordinate of the graph represents impedance values and the abscissa of the graph represents time. FIG. 16a depicts a schematic plot of an embodiment of an impedance curve obtained from a patient in whom a gastrointestinal leak is not present. Impedance value determination may be initiated at a time equal to zero prior to the administration of contrast solution to obtain a baseline impedance value 650. While impedance measuring continues, contrast solution may be introduced to the gastrointestinal tract at a time i. A deviation from the baseline impedance value is not observed in the impedance curve 660 and it may be concluded that salt contrast solution did not come into contact with sensors of the flexible conduit. Therefore, a gastrointestinal leakage may not be present in this patient. In FIG. 16a, impedance is monitored until a pre-determined time x, at which point monitoring impedance ceases. In FIG. 16a, the integral of the quantified anastomotic leak value given by Equation 1 may yield a value of zero.

FIG. 16b depicts a schematic plot of an embodiment of an impedance curve obtained from a patient with a gastrointestinal leak. Impedance value measurement may be initiated at a time equal to zero prior to the administration of a contrast solution to obtain a baseline impedance value 650. Impedance continues to be measured while a contrast solution may be introduced into the gastrointestinal tract at a time i. A deviation from the baseline impedance value may be observed in the impedance curve 660 leading to the conclusion that contrast solution contacted a sensor of the flexible conduit. A gastrointestinal leak may be present in this patient.

In FIG. 16b, the measured impedance values after the administration of a contrast solution may reach a maximum deviation 670 from the baseline impedance value 650 after which a gradual return to baseline impedance value may be observed. Impedance value determination may continue until a pre-determined time x, at which point impedance value measurement ceases. Since a gastrointestinal leak may be present and a deviation in impedance after the administration of a contrast solution is observed, the integral of the quantified anastomotic leak value 680 given by Equation 1 may yield a non-zero value that quantifies the leak.

Figure 17:
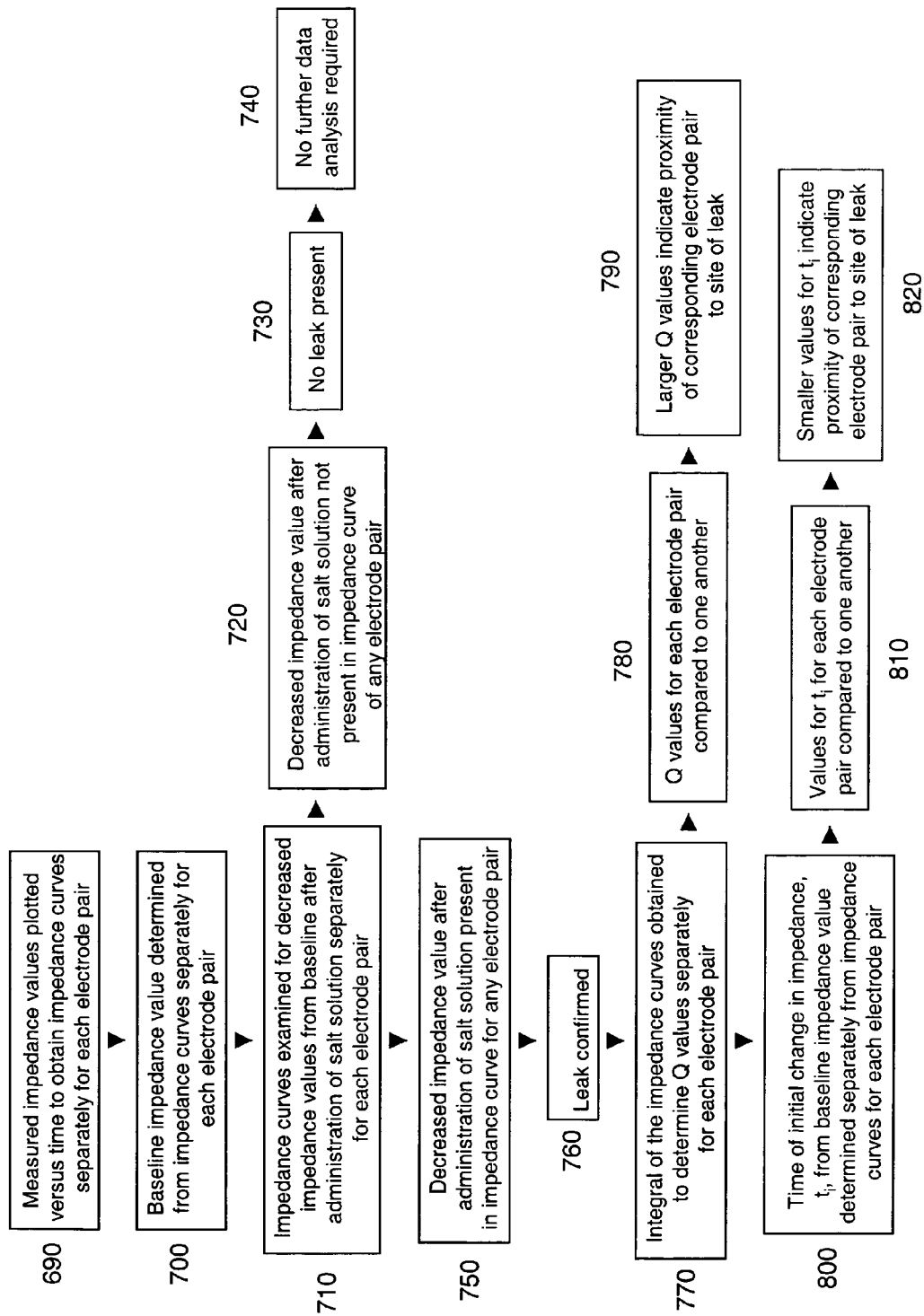
FIG. 17 depicts a process flow diagram of a method of analyzing data obtained by an embodiment of a physiological change monitoring system with more than one sensor.

FIG. 17 depicts a process flow diagram of a method of analyzing data obtained by an embodiment of a physiological change monitoring system with more than one sensor. Impedance values obtained by each pair of sensors and measured by the impedance measurement unit over the pre-determined time period may be plotted versus time to obtain separate impedance curves for each sensor pair 690. The impedance values observed from the region of the impedance curve corresponding to the measurements recorded prior to the administration of a contrast solution may be the baseline impedance values 700. Baseline impedance values may be determined separately for each pair of sensors. Impedance curves for each sensor pair may be examined for changes in impedance values after a time corresponding to the administration of a contrast solution 710. When changes in impedance are not observed in the impedance curves for any of the sensor pairs 720, a gastrointestinal leak may not be present 730. Further data collection may not be necessary in the absence of a detected gastrointestinal leak 740. When changes in impedance values are observed in the impedance curve generated by one or more of the sensor pairs 750, a gastrointestinal leak may be present 760. A value for the quantified anastomotic leak, Q, may be obtained for each impedance curve generated by a pair of sensors based on the integral of the impedance curve obtained by using Equation 1 or Equation 2 770. Q values obtained for each impedance curve generated by a sensor pair may be compared to Q values of other sensor pairs in terms of relative magnitude 780. Impedance curves with the largest Q values may indicate that a corresponding sensor pair may be proximate the site of the gastrointestinal leak 790. The time, $t_i$, of the initial change in impedance from baseline observed after administration of a contrast solution may be determined from the impedance curves for each sensor pair separately 800. The values of $t_i$ obtained for each pair of sensors may be compared to the values obtained for other pairs of sensors 810. Smaller values of $t_i$ may indicate sensor proximity to the gastrointestinal leak 820.

FIGS. 18a-c depict schematic plots of impedance values obtained by an embodiment of a physiological change monitoring system with three electrode pairs as sensors. FIGS. 18a-c illustrate how differential impedance curves generated by the various electrode pairs may be used to identify the site of a gastrointestinal leak. In the schematic plots shown in FIGS. 18a-c, the ordinate of all plots represents impedance and the abscissa of all plots represents time. In FIGS. 18a-c, each individual plot represents the impedance measurements of a single electrode pair obtained simultaneously for each electrode pair. Indicated on the abscissa are time points: 0, the time at which impedance measurement is initiated; i, the time at which a contrast solution is introduced into the gastrointestinal tract; and x, the time at which impedance measurement is terminated. The time points may represent the same moments in time for measurements obtained from each of the electrode pairs. Measurements may be obtained simultaneously for each electrode pair. FIG. 18a depicts an impedance curve generated by the impedance values measured by an embodiment of a first electrode pair, EP1. From the impedance curve 660 for EP1, values may be obtained for the following: baseline impedance 650; $t_{i1}$, the earliest moment in time at which a deviation in impedance measurement from the baseline impedance may be detected by EP1; and $Q_1$ 680, the integral of the impedance curve of EP1 calculated using Equation 1 or Equation 2. FIG. 18b depicts an impedance curve generated by the impedance values measured by an embodiment of a second electrode pair, EP2. From the impedance curve 660 for EP2, values may be obtained for the following: baseline impedance 650; $t_{i2}$, the earliest moment in time at which a deviation in impedance measurement from the baseline impedance may be detected by EP2; and $Q_2$ 680, the integral of the impedance curve of EP2 calculated using Equation 1 or Equation 2. FIG. 18c depicts an impedance curve generated by the impedance values measured by a third electrode pair, EP3. From the impedance curve 660 for EP3, values may be obtained for the following: baseline impedance 650; $t_{i3}$, the earliest moment in time at which a deviation in impedance measurement from the baseline impedance may be detected by EP3; and $Q_3$ 680, the integral of the impedance curve of EP3 calculated using Equation 1 or Equation 2. In FIGS. 18a-c, the electrode pair that produces the lowest value for $t_i$ may be the electrode pair closest to the area of the gastrointestinal leak since the closest electrode pair may be the first to contact leaking contrast solution. In FIGS. 18a-c, $t_{i1} < t_{i2} < t_{i3}$, indicating that in this example the electrode pairs listed in order of closeness in proximity to the area of the leak are: EP1, EP2, EP3. In FIGS. 18a-c, the electrode pair that produces the greatest value for Q 680 may be the electrode pair closest to the area of gastrointestinal leak because the closest electrode pair may contact the greatest volume of leaking contrast solution and/or will remain in contact with leaking contrast solution for the greatest period of time, relative to the other electrode pairs. In FIGS. 18a-c, $Q_1 > Q_2 > Q_3$, indicating that in this example the electrode pairs listed in order of closeness in proximity to the area of the leak are: EP1, EP2, EP3.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the spirit and scope of the invention as described in the following claims. In addition, it is to be understood that features described herein independently may, in certain embodiments, be combined.

What is claimed is:

1. A leak monitoring system comprising:
a flexible conduit, wherein the flexible conduit is, during use, positioned inside of an opening in a human body, and wherein the flexible conduit comprises one or more channels;
one or more sensors disposed in or on, or connected to, the flexible conduit, wherein at least one of the sensors, during use, senses impedance changes caused by one or more fluids, introduced into the body part, leaking from the body part and contacting the one or more impedance sensors; and
an electrical conduit connected to provide electrical signals from one or more of the impedance sensors to a measurement determining unit, wherein the measurement determining unit determines, during use, the impedance change due to the presence of at least one fluid leaking from the body part;
wherein fluid leaking from the body part flows through one or more channels in the flexible conduit.

2. The system of claim 1, wherein the measurement determining unit determines the presence of a leak when an impedance decrease is detected in one or more of the impedance sensors.

3. The system of claim 1, wherein the flexible conduit is positionable proximate a hollow organ, and wherein at least one sensor directly measures impedance_changes proximate of the hollow organ.

4. The system of claim 1, wherein at least one channel comprises a groove.

5. The system of claim 1, wherein at least one channel is corrugated.

6. The system of claim 1, wherein a portion of a cross sectional area of the flexible conduit is convex.

7. A method of detecting leaks in a body part comprising:
inserting a flexible conduit in an opening in the body, wherein the flexible conduit comprises two or more sensors disposed in or on, or connected to, the flexible conduit, wherein at least one of the sensors, during use, senses impedance changes proximate to the body part, and wherein the flexible conduit further comprises one or more channels wherein fluid leaking from the body part flows through one or more channels in the flexible conduit;
positioning the flexible conduit in the body proximate to a body part such that the two or more sensors are proximate the body part;
introducing a fluid into the body, wherein the fluid comprises one or more ions; and
monitoring the status of the two or more sensors after the fluid is introduced into the body, wherein a change in the impedance of one or more of the impedance sensors indicates the presence of a leak from the body part.

8. The method of claim 7, wherein introducing the fluid comprises:
allowing a patient to ingest the fluid;
allowing the fluid to flow through the body; and
wherein monitoring the status of the two or more sensors comprises allowing sufficient time for the fluid to pass to the body part before determining if a leak from the body part is present.

9. The method of claim 7, wherein the fluid is a saline solution.

10. The method of claim 7, further comprising:
transmitting the change in the impedance of one or more of the impedance sensors to a measurement detection unit;

comparing the change in the impedance of one or more of the impedance sensors to a base line value of the impedance proximate to the body part; and producing a signal when the change in the impedance of one or more of the impedance sensors deviates greater than a selected range from the base line value.

11. A leak monitoring system comprising:

a flexible conduit, wherein the flexible conduit is, during use, positioned inside of an opening in a human body, and wherein the flexible conduit comprises one or more channels;

one or more sensors disposed in, or on, or connected to, the flexible conduit, wherein at least one of the sensors, during use, senses ion concentration changes caused by one or more fluids, introduced into the body part, leaking from the body part and contacting the ion concentration sensor, and wherein ions measured by the ion concentration sensor comprise fluoride, bromide, carbonate, bicarbonate, potassium, copper, lead, silver, gold, sulfide, nitrate, ammonium, iodide, or calcium; and an electrical conduit connected to provide electrical signals from one or more of the ion concentration sensors to a measurement determining unit, wherein the measurement determining unit determines, during use, ion concentration changes due to the presence of at least one fluid leaking from the body part;

wherein fluid leaking from the body part flows through one or more channels in the flexible conduit.

12. The system of claim 1, wherein at least one sensor is in substantially direct contact with the body part.

13. The system of claim 1, wherein the system is capable of being positioned in an opening in the body proximate to an esophagus.

14. The system of claim 1, wherein the system is capable of being positioned in an opening in the body proximate to a lung.

15. The system of claim 1, wherein the system is capable of being positioned in an opening in the body proximate to a portion of a gastrointestinal tract.

16. The system of claim 1, wherein the system is capable of being positioned in an opening in the body proximate to a stomach.

17. The method of claim 7, wherein at least one of the sensors, during use, senses ion concentration changes proximate to the body part, the method further comprising:

allowing a patient to ingest the fluid; and allowing the fluid to flow through the body;

wherein monitoring the status of the two or more sensors comprises allowing sufficient time for the fluid to pass to the body part before determining if a leak from the body part is present.

18. The method of claim 17, wherein the fluid is a solution containing dissolved ions, said dissolved ions being of a type and/or concentration out of physiological norms.

19. The system of claim 1, wherein body part is a body part subjected to a surgical procedure, and wherein flexible conduit is positionable proximate to the body part such that fluids leaking from the body part, as a result of the surgery, are sensed by one or more of the sensors.

20. The system of claim 1, wherein the body part is the stomach, and wherein the flexible conduit is positionable proximate to the stomach such that fluids leaking from the stomach are sensed by one or more of the sensors.

21. The method of claim 7, wherein the flexible conduit is positioned proximate to a portion of a gastrointestinal tract.

22. The method of claim 7, wherein the flexible conduit is positioned proximate to a portion of a gastrointestinal tract after a surgical procedure, wherein monitoring the status of two or more sensors comprises monitoring leakage of the fluid from the gastrointestinal portion.

* * * * *